US011602724B2

(12) United States Patent
Chintala et al.

(10) Patent No.: US 11,602,724 B2
(45) Date of Patent: Mar. 14, 2023

(54) VISIBLE LIGHT INDUCED PHOTOGENERATION OF GROUND STATE ATOMIC OXYGEN

(71) Applicant: Saint Louis University, St. Louis, MO (US)

(72) Inventors: Satyanarayana M. Chintala, St. Louis, MO (US); Ryan D. McCulla, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 194 days.

(21) Appl. No.: 16/863,109

(22) Filed: Apr. 30, 2020

(65) Prior Publication Data

US 2020/0346183 A1 Nov. 5, 2020

Related U.S. Application Data

(60) Provisional application No. 62/841,075, filed on Apr. 30, 2019.

(51) Int. Cl.
*C07D 345/00* (2006.01)
*B01J 19/12* (2006.01)
*C01B 13/02* (2006.01)

(52) U.S. Cl.
CPC ......... *B01J 19/123* (2013.01); *C01B 13/0222* (2013.01); *C07D 345/00* (2013.01)

(58) Field of Classification Search
CPC .............. B01J 19/123; C01B 13/0222; C07D 345/00
See application file for complete search history.

(56) References Cited

U.S. PATENT DOCUMENTS

2010/0072887 A1 3/2010 Kwong et al.

OTHER PUBLICATIONS

Tezuka, T., "Photochemical transfer of oxygen from selenoxide to sulfide." Tetrahedron Letters 19.49 (1978): 4885-4886.*
Bommel 2012_Encyclopedia of Color Science and Technology p. 1-5.pdf.*
Corning-Pyrex 1987 p. 1-14.*
Alam, A., et al., "A new method for the synthesis of dinaptho[1,2-b;2',1'-d]thiophenes and selenophenes," 2007, Heteroatom Chemistry, 18/3:239-248, 11 pages.
Bourdillon, M. T., et al., "Oxidation of Plasmalogen, Low-Density Lipoprotein, and RAW 264.7 Cells by Photoactivatable Atomic Oxygen Precursors," 2014, Photochem. Photobiol. 90/2:386-393, 18 pages.
Bucher, G., et al., "Laser Flash Photolysis of Pyridine N-Oxide: Kinetic Studies of Atomic Oxygen [O(3P)] in Solution," 1994, J. Phys. Chem. 98/1:12471-12473, first page only.

Chintala et al., "Visible light initiated photogeneration of [O(3P)] in condensed phases," 2018, ACS Midwest Poster Presentation, 1 page.
Chintala et al., "Benzo[b]naphtho[2,1-d]selenophene-Se-oxide, Benzo[b]naphtho[1,2-d]selenophene-Se-oxide as potential O(3P) precursors," 2017, ACS Midwest Poster Presentation, 1 page.
De Lucas N.C., et al., "A Laser Flash Photolysis Study of Dibenzothiophene Sulfoxide and benzo[b]napto[2,1-d] thiophene-11-oxide," 2007, J.Photochem. Photobiol. A: Chemistry, 188:293-297.
Gregory, D.D., et al., "Photodeoxygenation of Dibenzothiophene Sulfoxide: Evidence for a Unimolecular S—O Cleavage Mecanism," 1997, J. Am. Chem. Soc., 19/1:94-102, Abstract only, 1 page.
Gurria, G. M., et al., "Photochemical Deoxygenation of Aryl Sulfoxides," J. Org. Chem. 1973, 38/13:2-2419-2420, first page only.
Kirsch G., et al., "Palladium-catalyzed coupling reaction of 3-bromo benzo[b]furan, -thiophene and selenophene 2-carboxaldehyde. Preparation of tetracyclic heteroaromatic derivatives," 2006, Z. Naturforsch, Journal of Chemical Sciences, 61(b):427-430.
Klaning, U. K., et al., "Ozone Formation in Laser Flash Photolysis of Oxoacids and Oxoanions of Chlorine and Bromine", 1984, Chem. Soc., Faraday Trans, 80:2969-2979, Abstract Only, 1 page.
Korang, J., et al., "Photoinduced DNA Cleavage by Atomic Oxygen Precursors in Aqueous Solutions," 2013, RSC Adv., 3/30:12390-12397, Abstract Only, 1 page.
Lucien, E., et al., "Electrophilic Oxidant Produced in the Photodeoxygenation of 1,2-Benzodiphenylene Sulfoxide," 2001, J. Org. Chem., 600:4576-4579, 4 pages.
McCulla et al., "Deoxygenation and other Photochemical Reactions of Aromatic Selenoxides," 2004, J. Am. Chem. Soc. 126/49:16058-16065, 10 pages.
Omlid, S. M, et al., "Thiol Reactivity toward Atomic Oxygen Generated During the Photodeoxygenation of Dibensothiophene S-Oxide," 2017, J. Org. Chem., 82 (24), 12947-12966, Abstract Only, 1 page.
Paegle, E., et al., "An Approach to the Selenobromination of Aryl(thienyl)alkynes: Access to 3-Bromobenzo[b] selenophenes and Selenophenothiophenes," 2014, European J. Org. Chem., 2014/18, 3831-3840, Abstract only, 1 page.
Rockafellow, E.M., et al., "Deoxygenation of dibenzothiophene-S-oxide and dibenzoselenophene-Se-oxide: A comparison of direct and sensitized photolysis," 2008, J of Photochem and Photobiology A: Chemistry, 198:45-51, 7 pages.
Stoffregen, S.A., et al., "Computational investigation of the photochemical deoxygenation of thiophene-S-oxide and selenophene-Se-oxide," 2014, Photochemical and Photobiological Sciences., 13:431-438, 10 pages.
Thomas, K.B., et al., "Gauging the Significance of Atomic Oxygen [O(3P)] in Sulfoxide Photochemistry. A Method for Hydrocarbon Oxidation," 2003, J. Org. Chem., 68/5:1886-1891, 6 pages.
Zhang, M.; Ravilious, G. E.; Hicks, L. M.; Jez, J. M.; McCulla, R. D. "Redox switching of adenosine-5'-phosphosulfate kinase with photoactivatable atomic oxygen precursors" J. Am. Chem. Soc. 2012, 134 (41), 16979-16982, Abstract Only, 1 page.
Zheng, X., et al., "Photodeoxygenation of Dinaphthothiophene, Benzophenanthrothiophene, and Benzonaphthothiophese S-Oxides," 2016, Photochem. Photobiol. Sci An Int. J. 2016, 791-800, 10 pages.

* cited by examiner

*Primary Examiner* — John M Mauro

(74) *Attorney, Agent, or Firm* — Stinson LLP

(57) ABSTRACT

The present invention generally relates to various polycyclic aromatic selenoxide compounds, methods for preparing these compounds, and methods of us these and other compounds to generate ground state atomic oxygen.

18 Claims, 2 Drawing Sheets

A.

B.

VISIBLE LIGHT INDUCED PHOTOGENERATION OF GROUND STATE ATOMIC OXYGEN

REFERENCE TO RELATED APPLICATIONS

This application claims the benefit of U.S. Provisional Application Ser. No. 62/841,075, filed Apr. 30, 2019, the contents of which are incorporated by reference herein.

STATEMENT REGARDING FEDERALLY SPONSORED RESEARCH OR DEVELOPMENT

This invention was made with Government support under CHE-1255270 awarded by the National Science Foundation. The Government has certain rights in the invention.

FIELD OF THE INVENTION

The present invention generally relates to various dibenzoselenophene compounds, methods for preparing these compounds, and methods of these compounds and other compounds to generate ground state atomic oxygen.

BACKGROUND OF THE INVENTION

Ground state atomic oxygen [$O(^3P)$] is an important oxidant because of its selective reactivity and strong oxidative properties. The reactivity of $O(^3P)$ has been investigated extensively in the gas phase due to its importance in industrial and environmental chemistry. The widely used methods for producing $O(^3P)$ in gas phase are decomposition of $N_2O$ by mercury photosensitization, photolysis of liquid carbon dioxide by γ-rays, microwave discharge of helium and molecular oxygen mixture. In contrast to the gas phase, the reactivity of $O(^3P)$ in the condensed phase is yet to be thoroughly explored due to the dearth of clean and efficient methods of generation of $O(^3P)$ in the condensed phase.

Photodeoxygenation of certain aryl sulfoxides is a method for generating $O(^3P)$ in solution. Other sources of $O(^3P)$ in the condensed phase include photodeoxygenation of dibenzoselenophene Se-oxide (DBSeO), pyridine N-oxide, and oxo-anions. Irradiation of pyridine N-oxide with 308 nm light yields ninety five percent oxaziridine and only five percent $O(^3P)$ and pyridine. Photodeoxygenation of DBSeO generates $O(^3P)$ and dibenzoselenophene (DBSe), but also yields the undesired selenic ester as shown below.

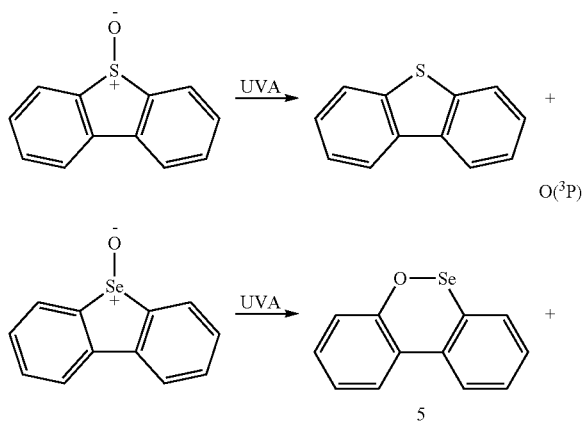

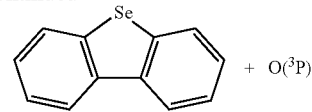

Photolysis of oxo-anions produces $O(^3P)$, but requires 193 nm, 248.5 nm or 308 nm wavelength light and generates ozone as a byproduct. Photodeoxygenation of dibenzothiophene S-oxide (DBTO) is a clean source of $O(^3P)$ as it produces solely $O(^3P)$ and dibenzothiophene (DBT). However, this method requires high energy UVA irradiation and has a low quantum yield of photodeoxygenation of 0.003.

In the condensed phase, $O(^3P)$ has been shown to cause deoxyribonucleic acid (DNA) strand scission in plasmid DNA and selectively oxidize cysteine residues of adenosine-5'-phosphosulfate kinase (APSK). The oxidation of low density lipoprotein (LDL) by $O(^3P)$ yielded primarily fatty aldehydes. Additionally, $O(^3P)$ selectively oxidizes tertiary carbon of 2-methyl-butane to the corresponding alcohol and benzene to phenol. These results show $O(^3P)$ could be a potential oxidant in organic synthesis and for probing biological pathways.

Despite the advantages of utilizing $O(^3P)$, the necessity of UVA light combined with low photodeoxygenation quantum yields of currently available $O(^3P)$ generation methods have hindered the application of $O(^3P)$ in organic synthesis and biochemistry. Thus, there is a need for cleaner, more efficient and higher yielding methods of generating $O(^3P)$.

BRIEF SUMMARY OF THE INVENTION

The present invention generally relates to various polycyclic aromatic selenoxide compounds, methods for preparing these compounds, and methods of using of these and other compounds to generate ground state atomic oxygen.

Various aspects of the invention relate to methods for producing ground state atomic oxygen ([$O(^3P)$] comprising illuminating a mixture comprising a polycyclic aromatic selenoxide and an oxygen accepting substrate with visible or invisible light to produce ground state atomic oxygen and an oxidation product.

Further aspects of the invention are directed to compounds having the structure of Formula (Ia) or (Ib):

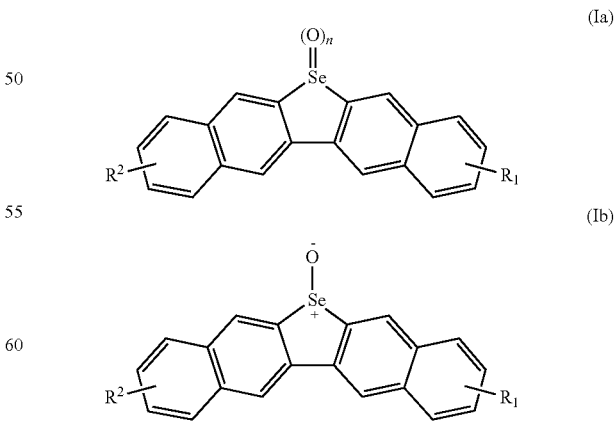

wherein $R^1$ and $R^2$ are each independently hydrogen, hydroxyl, substituted or unsubstituted hydrocarbyl, or substituted or unsubstituted amino and n is 1 or 2.

Other aspects of the invention are directed to compounds having the structure of Formula (IIa) or (IIb):

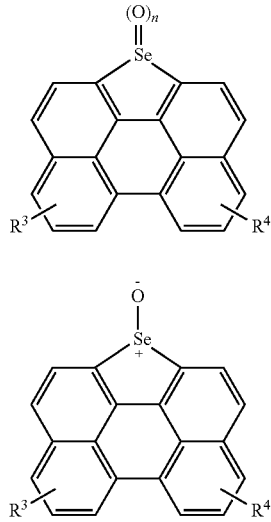

wherein $R^3$ and $R^4$ are each independently hydrogen, hydroxyl, substituted or unsubstituted hydrocarbyl, or substituted or unsubstituted amino and n is 1 or 2.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE INVENTION

Figure 1A:
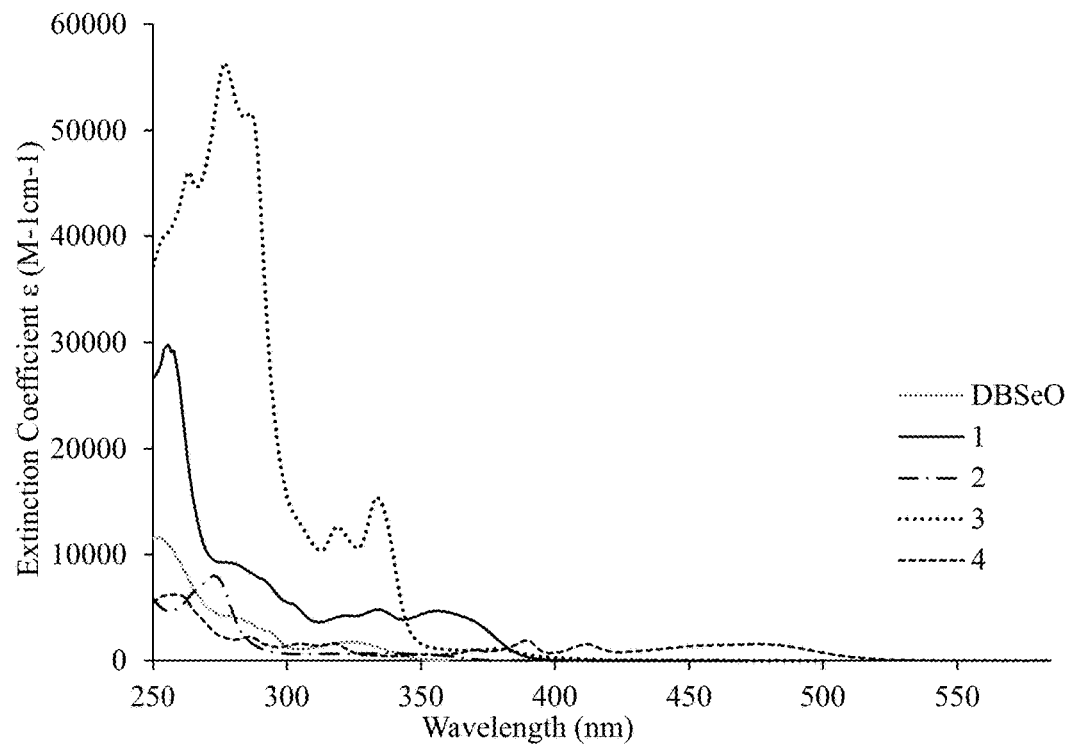
FIG. 1A is a plot of the extinction coefficient ($M^{-1}cm^{-1}$) at different wavelengths for DBSeO and compounds 1-4.

In general, the present invention is directed to various polycyclic aromatic selenoxides, methods for preparing these compounds, and methods for generating $O(^3P)$. Notably, various compounds described herein deoxygenate in visible light or near-visible light and have high quantum yields of photodeoxygenation. The compounds and methods described herein can greatly reduce photodeoxygenation reaction time and since they require only visible light or near-visible light, which is benign compared to UVA. Advantageously, the compounds and methods described herein can create a lower barrier to adoption of $O(^3P)$ in other fields.

Various compounds described herein comprise polycyclic aromatic selenoxides. In various embodiments, the polycyclic aromatic selenoxides have the structure of Formula (Ia) or (Ib):

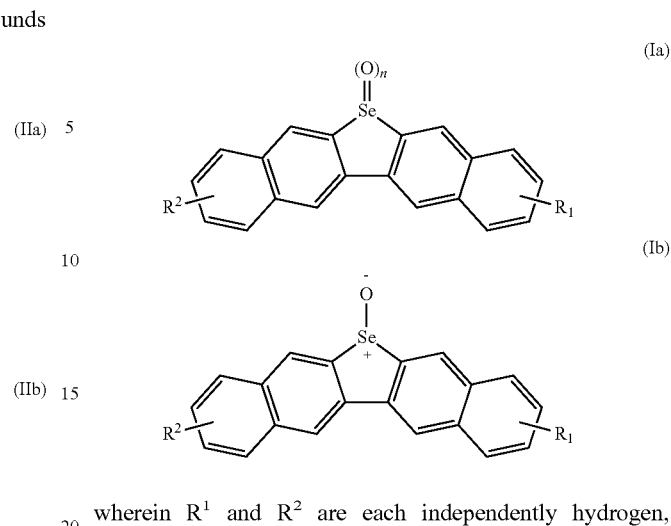

wherein $R^1$ and $R^2$ are each independently hydrogen, hydroxy, substituted or unsubstituted hydrocarbyl, or substituted or unsubstituted amino and n is 1 or 2. When n is 2, the compound of Formula (Ia) can be represented by the compound of Formula (Ib) where the single bond reflects the fact that the selenoxide can be a chiral center and that the double bond is in resonance form.

In some embodiments, $R^1$ and $R^2$ are each independently hydrogen, hydroxy, $C_1$-$C_{20}$ alkyl, $C_1$-$C_{20}$ alkoxy, $C_1$-$C_{20}$ haloalkyl, $C_1$-$C_{20}$ haloalkoxy, substituted or unsubstituted $C_2$-$C_{20}$ alkenyl, substituted or unsubstituted $C_2$-$C_{20}$ alkynyl, substituted or unsubstituted aryl, or substituted or unsubstituted heteroaryl. In certain embodiments, $R^1$ and $R^2$ are each independently hydrogen, hydroxy, $C_1$-$C_{10}$ alkyl, $C_1$-$C_{10}$ alkoxy, $C_1$-$C_{10}$ haloalkyl, $C_1$-$C_{10}$ haloalkoxy, halo-substituted $C_1$-$C_{10}$ alkenyl, halo-substituted $C_2$-$C_{10}$ alkynyl, aryl, alkyl-substituted aryl, halo-substituted aryl, or hydroxy-substituted aryl.

In various embodiments, $R^1$ and $R^2$ are each independently hydrogen, hydroxy, methyl, ethyl, butyl, methoxy, ethoxy, propoxy, trifluoromethyl, phenyl, hydroxyphenyl, ethylphenyl, carboxyphenyl, napthyl, anthracenyl, biphenyl, tolyl, cumyl, styryl, orth-xylyl, meta-xylyl, para-xylyl, fluorphenyl, chlorophenyl, bromophenyl, or iodobenzyl. In some embodiments, $R^1$ and $R^2$ are each hydrogen.

In certain embodiments, the polycyclic aromatic selenoxide having the structure of Formula (Ia) or (Ib) is dinaphtho [2,3-b:2',3'-d]selenophene 6-oxide:

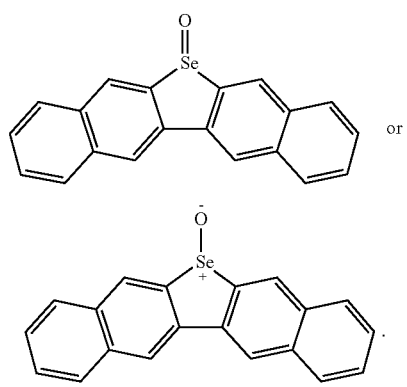

Various methods of preparing the polycyclic aromatic selenoxides of Formula (I) comprise one or more of the following steps:

(a) reacting, in the presence of an organic solvent n-butyl-lithium with one or more 2,3-dibromonaphthalenes (Formulas (A-1) and (A-2))

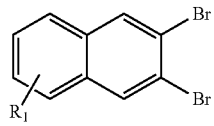
(A-1)

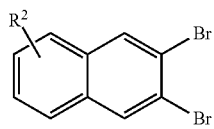
(A-2)

to form a 3,3'-dibromo-2,2'-binapththalene of Formula (A-3):

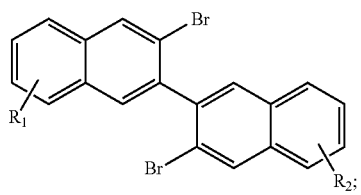
(A-3)

(b) reacting the 3,3'-dibromo-2,2'-binapthalene of Formula (A-3) with t-butyl-lithium in an anhydrous organic solvent, selenium and sulfuryl chloride to form the selenophene compound of Formula (A-4):

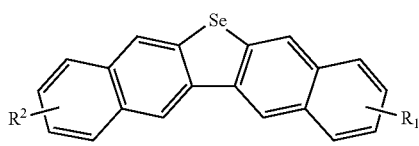
(A-4)

wherein $R^1$ and $R^2$ are as defined above for Formula (Ia) or (Ib). A further oxidation step can be performed to yield the compounds of Formula (I). The oxidation can be performed using an oxidant such as meta-chloroperoxybenzoic acid.

Other polycyclic aromatic selenoxide compounds of the present invention include compounds of Formula (IIa) or (IIb):

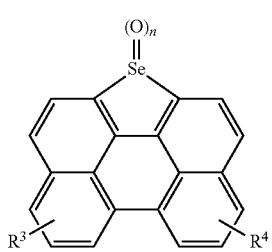
(IIa)

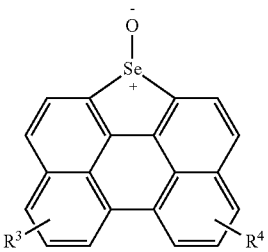
(IIb)

wherein $R^3$ and $R^4$ are each independently hydrogen, hydroxy, substituted or unsubstituted hydrocarbyl, or substituted or unsubstituted amino and n is 1 or 2. When n is 2, the compound of Formula (IIa) can be represented by the compound of Formula (IIb) where the single bond reflects the fact that the selenoxide can be a chiral center and the double bond is in resonance form.

In various embodiments, $R^3$ and $R^4$ are each independently hydrogen, hydroxy, $C_1$-$C_{20}$ alkyl, $C_1$-$C_{20}$ alkoxy, $C_1$-$C_{20}$ haloalkyl, $C_1$-$C_{20}$ haloalkoxy, substituted or unsubstituted $C_2$-$C_{20}$ alkenyl, substituted or unsubstituted $C_2$-$C_{20}$ alkynyl, substituted or unsubstituted aryl, or substituted or unsubstituted heteroaryl. In some embodiments, $R^3$ and $R^4$ are each independently hydrogen, hydroxy, $C_1$-$C_{10}$ alkyl, $C_1$-$C_{10}$ alkoxy, $C_1$-$C_{10}$ haloalkyl, $C_1$-$C_{10}$ haloalkoxy, halo-substituted $C_1$-$C_{10}$ alkenyl, halo-substituted $C_2$-$C_{10}$ alkynyl, aryl, alkyl-substituted aryl, halo-substituted aryl, or hydroxy-substituted aryl.

In certain embodiments, $R^3$ and $R^4$ are each independently hydrogen, hydroxy, methyl, ethyl, butyl, methoxy, ethoxy, propoxy, trifluoromethyl, phenyl, hydroxyphenyl, ethylphenyl, carboxyphenyl, napthyl, anthracenyl, biphenyl, tolyl, cumyl, styryl, orth-xylyl, meta-xylyl, para-xylyl, fluorphenyl, chlorophenyl, bromophenyl, or iodobenzyl. In some embodiments, $R^3$ and $R^4$ are each hydrogen.

In particular embodiments, the polycyclic aromatic selenoxide having the structure of Formula (IIa) or (IIb) is peryleno[1,12-bcd]selenophene 1-oxide:

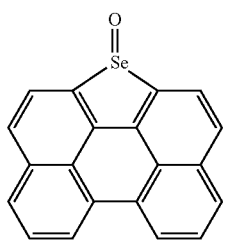 or 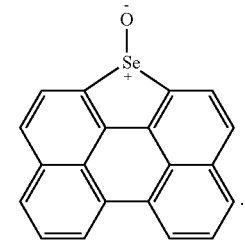.

Various methods of preparing the polycyclic aromatic selenoxides of Formula (II) comprise one or more of the following steps of:

(a) reacting nitrous acid with a perylene of Formula (B-1) in the presence of water and an organic solvent

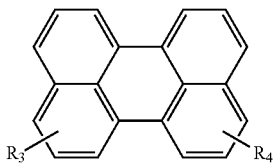

to form a nitrated perylene of Formula (B-2):

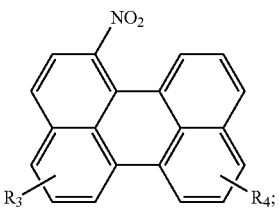

(a) reacting the perylene of Formula (B-2) with selenium in the presence of on organic solvent to form the selenophene of Formula (B-3):

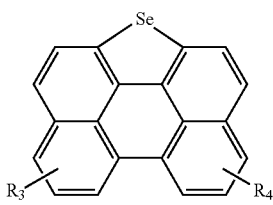

wherein $R^3$ and $R^4$ are as defined above for Formula (IIa) or (IIb). A further oxidation step can be performed to yield the compounds of Formula (II). The oxidation can be performed using an oxidant such as meta-chloroperoxybenzoic acid.

Other polycyclic aromatic selenoxide compounds include compounds of Formula (IIa) or (IIIb):

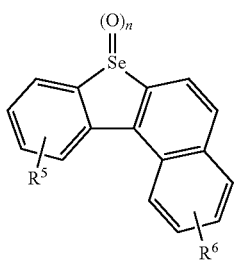

(IIIa)

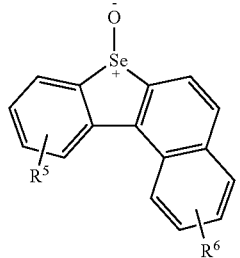

(IIIb)

wherein $R^5$ and $R^6$ are each independently hydrogen, hydroxy, substitute or, unsubstituted hydrocarbyl, or substituted or unsubstituted amino and n is 1 or 2. When n is 2, the compound of Formula (IIIa) can be represented by the compound of Formula (IIIb) where the single bond reflects the fact that the selenoxide can be a chiral center and the double bond is in resonance form.

In various embodiments, $R^5$ and $R^6$ are each independently hydrogen, hydroxy, $C_1$-$C_{20}$ alkyl, $C_1$-$C_{20}$ alkoxy, $C_1$-$C_{20}$ haloalkyl, $C_1$-$C_{20}$ haloalkoxy, substituted or unsubstituted $C_2$-$C_{20}$ alkenyl, substituted or unsubstituted $C_2$-$C_{20}$ alkynyl, substituted or unsubstituted aryl, or substituted or unsubstituted heteroaryl. In some embodiments, $R^5$ and $R^6$ are each independently hydrogen, hydroxy, $C_1$-$C_{10}$ alkyl, $C_1$-$C_{10}$ alkoxy, $C_1$-$C_{10}$ haloalkyl, $C_1$-$C_{10}$ haloalkoxy, halo-substituted $C_1$-$C_{10}$ alkenyl, halo-substituted $C_2$-$C_{10}$ alkynyl, aryl, alkyl-substituted aryl, halo-substituted aryl, or hydroxy-substituted aryl.

In certain embodiments, $R^5$ and $R^6$ are each independently hydrogen, hydroxy, methyl, ethyl, butyl, methoxy, ethoxy, propoxy, trifluoromethyl, phenyl, hydroxyphenyl, ethylphenyl, carboxyphenyl, napthyl, anthracenyl, biphenyl, tolyl, cumyl, styryl, orth-xylyl, meta-xylyl, para-xylyl, fluorphenyl, chlorophenyl, bromophenyl, or iodobenzyl. In some embodiments, $R^5$ and $R^6$ are each hydrogen.

In particular embodiments, the polycyclic aromatic selenoxide having the structure of Formula (IIIa) or (IIIb) is benzo[b]naphtho[1,2-d]selenophene 7-oxide:

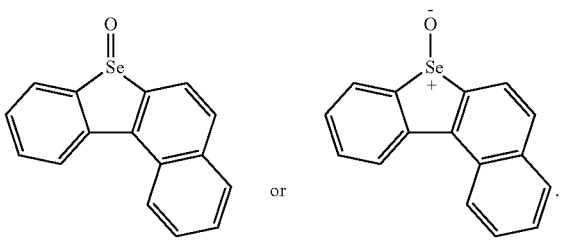

Various methods of preparing the polycyclic aromatic selenoxides of Formula (III) comprise one or more of the following steps of:

(a) reacting, in the presence of a catalyst comprising palladium, a base, and organic solvent, a 3-bromobenzo[b]selenophene-2-carbaldehyde of Formula (C-1) with a (2-formylphenyl)boronic acid of Formula (C-2):

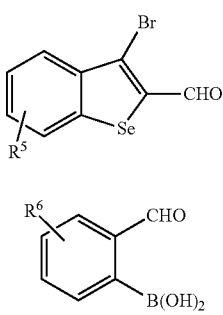
(C-1)

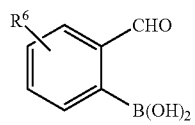
(C-2)

to form a 3-(2-formylphenyl)benzo[b]selenophene-2-carbaldehyde compound of Formula (C-3):

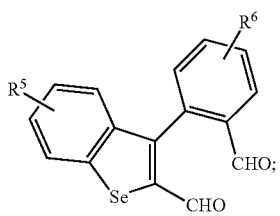
(C-3)

and (b) reacting the compounds of Formula (C-3) with titanium chloride and zinc in an organic solvent to form the selenophene compound of Formula (C-4):

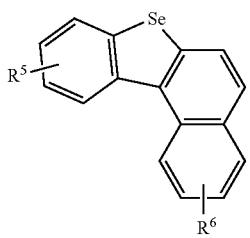
(C-4)

wherein $R^5$ and $R^6$ are as defined above for Formula (IIIa) or (IIIb). A further oxidation step can be performed to yield the compounds of Formula (III). The oxidation can be performed using an oxidant such as meta-chloroperoxybenzoic acid.

Other polycyclic aromatic selenoxide compounds include compounds of Formula (IVa) or (IVb):

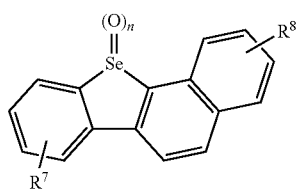
(IVa)

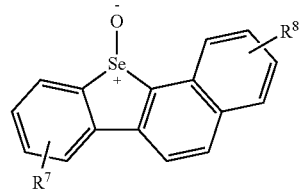
(IVb)

wherein $R^7$ and $R^8$ are each independently hydrogen, hydroxy, substituted or unsubstituted hydrocarbyl, or substituted or unsubstituted amino and n is 1 or 2. When n is 2, the compound of Formula (IVa) can be represented by the compound of Formula (IVb) where the single bond reflects the fact that the selenoxide can be a chiral center and the double bond is in resonance form.

In various embodiments, $R^7$ and $R^8$ are each independently hydrogen, hydroxy, $C_1$-$C_{20}$ alkyl, $C_1$-$C_{20}$ alkoxy, $C_1$-$C_{20}$ haloalkyl, $C_1$-$C_{20}$ haloalkoxy, substituted or unsubstituted $C_2$-$C_{20}$ alkenyl, substituted or unsubstituted $C_2$-$C_{20}$ alkynyl, substituted or unsubstituted aryl, or substituted or unsubstituted heteroaryl. In some embodiments, $R^7$ and $R^8$ are each independently be hydrogen, hydroxy, $C_1$-$C_{10}$ alkyl, $C_1$-$C_{10}$ alkoxy, $C_1$-$C_{10}$ haloalkyl, $C_1$-$C_{10}$ haloalkoxy, halo-substituted $C_1$-$C_{10}$ alkenyl, halo-substituted $C_2$-$C_{10}$ alkynyl, aryl, alkyl-substituted aryl, halo-substituted aryl, or hydroxy-substituted aryl.

In various embodiments, $R^7$ and $R^8$ are each independently hydrogen, hydroxy, methyl, ethyl, butyl, methoxy, ethoxy, propoxy, trifluoromethyl, phenyl, hydroxyphenyl, ethylphenyl, carboxyphenyl, napthyl, anthracenyl, biphenyl, tolyl, cumyl, styryl, orth-xylyl, meta-xylyl, para-xylyl, fluorphenyl, chlorophenyl, bromophenyl, or iodobenzyl. In some embodiments, $R^7$ and $R^8$ are each hydrogen.

In particular embodiments, the polycyclic aromatic selenoxide having the structure of Formula (IVa) or (IVb) is benzo[b]naphtho[2,1-d]selenophene 11-oxide:

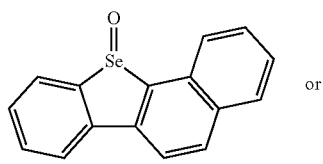
or

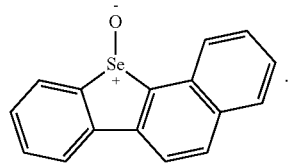

Various methods of preparing the polycyclic aromatic selenoxide of Formula (IV) comprise one or more of the following steps of:

(a) reacting, in the presence of an organic solvent and hydrogen bromide, cyclohexene, selenium oxide with a ethynylbenzene of Formula (D-1)

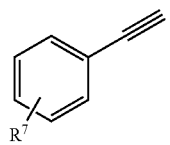

(D-1)

to form a substituted 3-bromobenzo[b]selenophene of Formula (D-2):

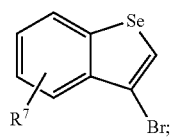

(D-2)

(b) reacting, in the presence of a catalyst comprising palladium, a base and an organic solvent, the compound of Formula (D-2) with a substituted (E)-styrylboronic acid of Formula (D-3):

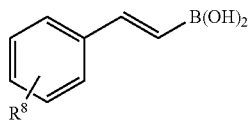

(D-3)

to form a substituted (E)-3-styrylbenzo[b]selenophene of Formula (D-4).

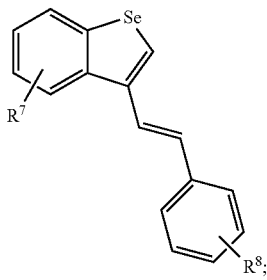

(D-4)

and (c) irradiating the compound of Formula (D-4) with UVA light in the presence of iodine and propylene oxide to form the selenophene compound of Formula (D-5)

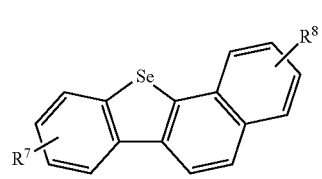

(D-5)

wherein $R^7$ and $R^8$ are as defined above for Formula (IVa) or (IVb). A further oxidation step can be performed to yield the compounds of Formula (IV). The oxidation can be performed using an oxidant such as meta-chloroperoxybenzoic acid.

As noted, the present invention also relates to methods of generating ground state atomic oxygen. Various methods comprise illuminating a mixture comprising a polycyclic aromatic selenoxide and an oxygen accepting substrate with visible or UV light to produce ground state atomic oxygen and an oxidation product.

In various embodiments, the polycyclic aromatic selenoxide is a compound of Formula (Ia), (Ib), (IIa), (IIb), (IIIa), (IIIb), (IVa), or (IVb):

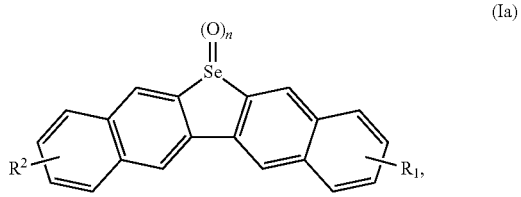

(Ia)

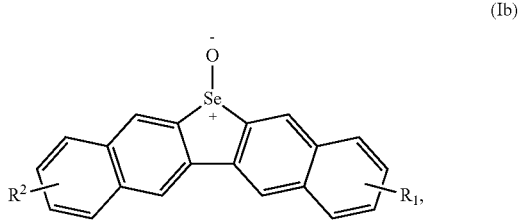

(Ib)

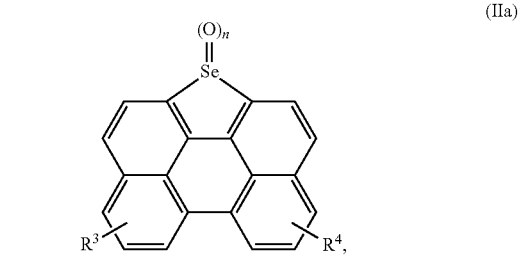

(IIa)

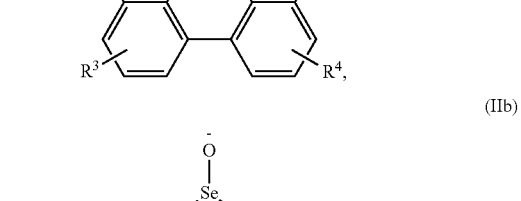

(IIb)

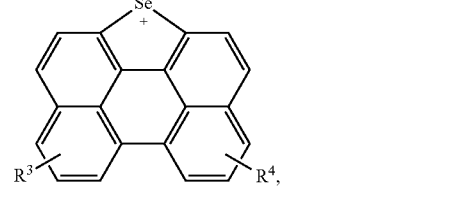

(IIIa)

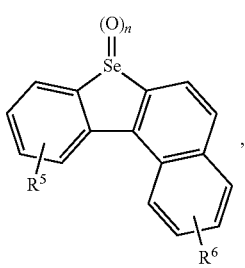

(IIIb)

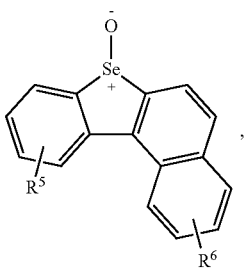

(IVa)

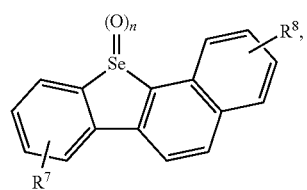

(IVb)

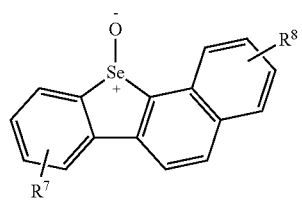

wherein R¹, R², R³, R⁴, R, R⁶, R⁷ and R⁸ and n are as defined above. In some embodiments, n is 1. In certain embodiments, the polycyclic aromatic selenoxide is:

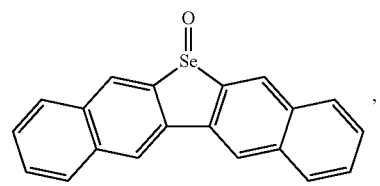

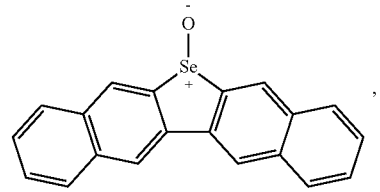

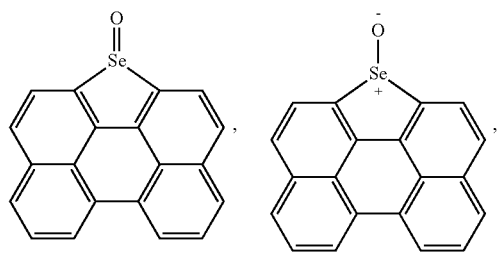

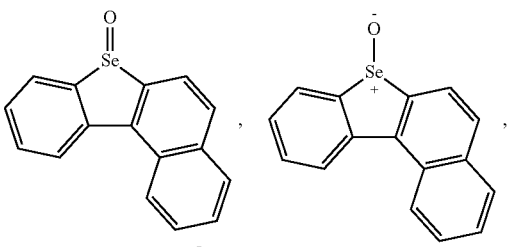

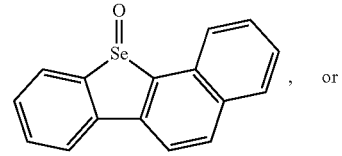

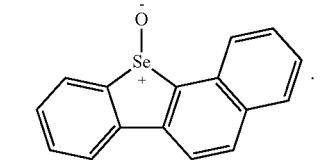

In various embodiments, the mixture is illuminated with visible light or near-visible light. In certain embodiments, the mixture is illuminated with light having a wavelength of from about 370 nm to about 900 nm, from about 370 nm to about 800 nm, from about 370 nm to about 740 nm, from about 380 nm to about 900 nm, from about 380 nm to about 800 nm, from about 380 nm to about 740 nm, from about 390 nm to about 900 nm, from about 390 nm to about 800 nm, or from about 390 nm to about 740 nm.

The oxygen accepting substrate can comprise, for example, an unsaturated hydrocarbon, an aromatic compound or a thiol. For example, the oxygen accepting substrate can comprise a substituted or unsubstituted $C_2$ to $C_{30}$ alkene or alkyne, a substituted or unsubstituted $C_5$-$C_{30}$ aryl, or substituted or unsubstituted $C_5$-$C_{30}$ heteroaryl, a thiol, or a $C_2$ to $C_{30}$ alkyl substituted thiol. For example, the oxygen accepting substrate can comprise a $C_2$ to $C_{10}$ alkene or alkyne, a $C_5$ to $C_6$ aryl or heteroaryl, or a $C_2$ to $C_{10}$ alkyl-substituted thiol. For instance, the substrate can comprise 1-octene, benzene, or toluene.

The methods of generating ground state atomic oxygen described herein, particularly those using visible light or near-visible light, can be applied in many biological or therapeutic contexts where use of higher energy (e.g., UV) light is detrimental. Recent findings suggest that $O(^3P)$ may cause DNA cleavage, lipid oxidation and initiate redox switching in proteins. These oxidative stressors may be exploited experimentally to study various cellular or molecular mechanisms or in therapies. Thus, in certain embodiments, the oxygen accepting substrate can be a biological specimen. For example, in some embodiments, the oxygen accepting substrate can comprise a nucleic acid, a protein or a lipid. The nucleic acid can be DNA or RNA.

Targeted damage to nucleic acids, lipids and/or proteins can trigger cell death pathways which can be advantageous in disease such as cancer. Advantageously, various compounds described herein can release ground state atomic oxygen upon irradiation from visible light, thereby limiting the secondary damage to nearby tissues or cells that can be caused by UV light. Thus, certain embodiments of the present invention comprise using the compounds and methods herein in chemotherapeutic applications to treat cancer.

Particularly envisioned are methods of oxidizing targets in vivo by generating the ground state atomic oxygen in situ using localized application of visible light or near-visible light. In various embodiments, the compound of Formula (Ia), (Ib), (IIa), (IIb), (IIIa), (IIIb), (IVa), or (IVb) can be applied to cells, tissues, or other living systems prior to irradiation.

In various embodiments, the mixture further comprises a solvent. The solvent can comprise, for example, acetonitrile, an alcohol or a buffer (e.g., a buffer suitable for the biological specimens described herein). In some embodiments, the alcohol is ethanol.

Definitions

Unless otherwise indicated, the alkyl, alkenyl, alkynyl, and alkoxy groups described herein preferably containing from 1 to 30 carbon atoms, from 1 to 20 carbon atoms, or from 1 to 10 carbon atoms in the principal chain. They can be straight chain (linear), branched chain, or cyclic. Also, unless otherwise indicated, the substituted alkyl, alkenyl, alkynyl, and alkoxy groups described herein can contain saturated or unsaturated and branched or unbranched carbon chains having from 1 to 20 carbon atoms or from 1 to 10 carbon atoms in the principal chain.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl (e.g., cyano), substituted cycloalkyl and the like.

Having described the invention in detail, it will be apparent that modifications and variations are possible without departing from the scope of the invention defined in the appended claims.

EXAMPLES

The following non-limiting examples are provided to further illustrate the present invention.

Materials.

All chemicals were purchased from Sigma Aldrich, Fisher, Arctom Chemicals, Oakwood chemicals or Ark Pharm and used without further purification except as specified. Anh. N-Methyl-2-pyrrolidone obtained from Sigma Aldrich was further dried using 3° A molecular sieves. HPLC grade toluene, benzene and acetonitrile were used for common intermediate experiments. Selenides 1Se-4Se, DBSe except for 2Se were synthesized according to the literature. Compounds 1-4, DBSeO and DBTO were synthesized by oxidizing 1Se-4Se, DBSe and DBT respectively. All the information about the synthesis of 1-4 is provided below in this section.

General Methods.

Shimadzu GC-2010 plus was used for GC-FID analysis. Absorption spectra were obtained using Shimadzu UV-1800 UV spectrophotometer. Bruker DRX-400 NMR was used to obtain NMR spectra of compounds 1-3. HPCL analysis was conducted using an Agilent 1200 Series HPLC with a quaternary pump, diode-array detector and a Higgins Analytical CLIPEUS C18 column (5 μm, 150×4.6 4.6 mm). Shimadzu GCMS equipped with QP2010S was used from GC-MS analysis.

Photodeoxygenation Quantum Yield Determination.

1-5 mM solutions of compounds 1-4 were prepared in HPLC grade acetonitrile or ethanol for determining the quantum yields of photodeoxygenation below 390 nm. Saturated solutions of 1 and 3 in ethanol were used for determining the quantum yields of photodeoxygenation at 400±3 nm. The optical densities of the prepared solutions were ensured to be greater than 2 at the desired wavelength for photolysis. 4.0 mL of prepared samples in quartz cuvettes (1 cm×1 cm) cells with long stem were degassed with argon for 10 min. The degassed solutions in quartz cuvettes were irradiated using a 75 W Xenon lamp focused on a monochromator (Photon Technologies International). The reactions were carried out to low conversions (<20%). HPLC was used to analyze the solutions before and after photolysis. Photorearrangement of azoxybenzene to 2-hydroxyazobenzene was used as an actinometer for wavelengths less than 390 nm, and for wavelengths above 390 nm, K[Cr(NH$_3$)$_2$(NCS)$_4$] was used.

Common Intermediate Experiments.

1-10 mM solutions of DBTO and compounds 1-4 were prepared. The solutions were sparged with argon in quartz cuvettes (1 cm×1 cm) with long stems. The degassed solutions were irradiated with either UVA bulbs (Luzchem LZC-UVA bulbs centered at 350 nm) or bulbs centered at 420 nm (Luzchem LZC-420 nm). The common intermediate experiments with 420 nm irradiation were also performed in glass test tubes. The changes in the concentrations of products were analyzed using GC-FID and changes in the concentration of DBT and corresponding selenides of 1-4 were analyzed using HPLC. Dodecane was used as an internal standard.

General Synthesis of Polycyclic Aromatic Selenoxides.

In the following Examples, the synthesis of polycyclic aromatic selenoxides 1-4 are described. The aryl selenoxides and selenides used throughout the examples are shown below.

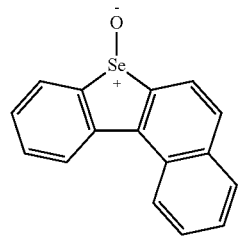

Benzo[b]naphtho[1,2-d] selenophene Se-oxide

1

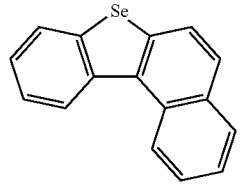

Benzo[b]naphtho[1,2-d] selenophene

1Se

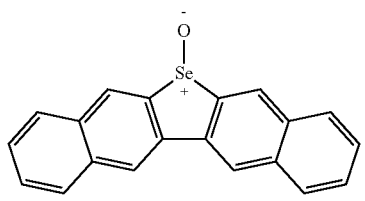

Dinaphtho[2,3-b:2',3'-d]
selenophene Se-oxide

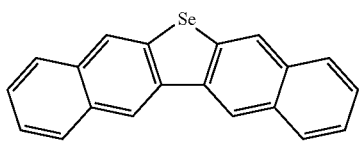

Dinaphtho[2,3-b:2',3'-d]
selenophene

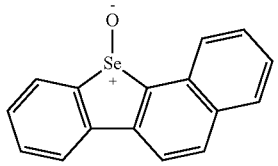

Benzo[b]naphtho[2,1-d]
selenophene Se-oxide

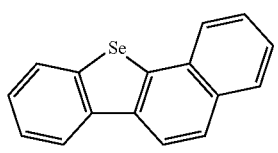

Benzo[b]naphtho[2,1-d]
selenophene

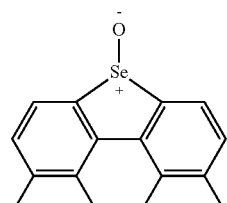

Perylo[1,12-b,c,d]selenophene
Se-oxide

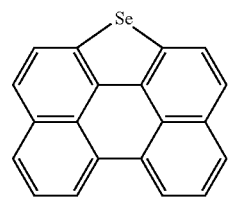

Perylo[1,12-b,c,d]selenophene

Compounds DBSeO, 1Se, 3Se and 4Se were synthesized according to previously reported procedures. Compounds 1 and 4 were prepared by oxidation of 1Se and 4Se respectively with 3-chloroperoxybenzoic acid (mCPBA) in dichloromethane (DCM). For selenide 4Se, the reported procedure yielded product only if anhydrous N-methyl-2-pyrrolidone (NMP) was used as the solvent.

The method for synthesis of DBSe has multiple steps. DBSe was prepared using a similar procedure to 3Se, which is a one-pot two steps process, as shown in Scheme 1. The synthesis of DBSe involved the reaction of 2,2'-dibromo-1,1'-biphenyl with tert-butyllithium (t-BuLi) at −78° C. in anhydrous tetrahydrofuran (THF) followed by addition of prepared SeCl$_2$, which was prepared by addition of selenium to SO$_2$Cl$_2$. DBSeO was obtained by oxidation of DBSe with mCPBA.

Scheme 1. Synthesis of compound DBSeO.

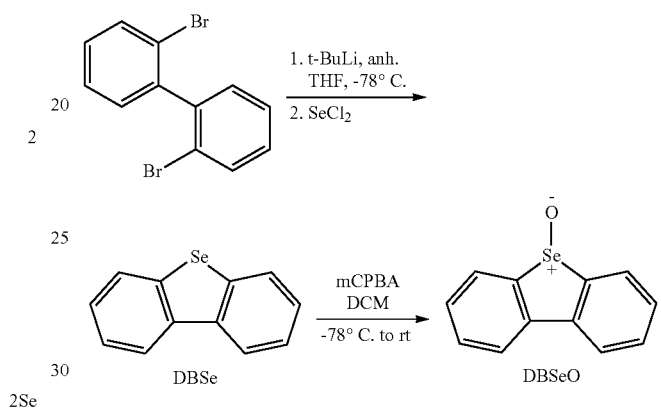

Selenoxide 2 was synthesized in four steps as shown in Scheme 2. The first step involved selenobromination of phenyl acetylene using HBr, SeO$_2$, and cyclohexene in 1,4-dioxane to yield 3-bromo-benzo[b]selenophene (2A). A Suzuki-Miyaura reaction was utilized in the second step for coupling trans-2-phenylvinylboronic acid with 2A to yield 3-(2-phenylethenyl)-benzo[b]selenophene (2B). Selenide, 2Se, was prepared by photocyclization of 2B in presence of iodine and propylene oxide under UVA irradiation. This method to synthesize 2Se has been previously used to prepare dinaphthothiophenes and benzonaphthothiophenes. The final step was oxidation of 2Se by mCPBA in DCM.

Scheme 2. Synthesis of compound 2.

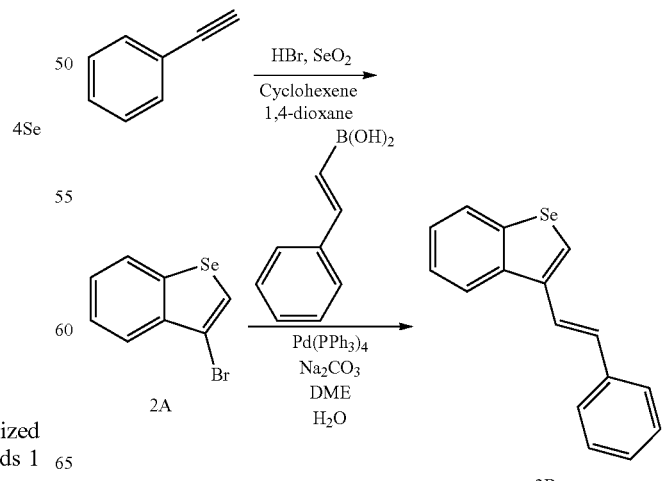

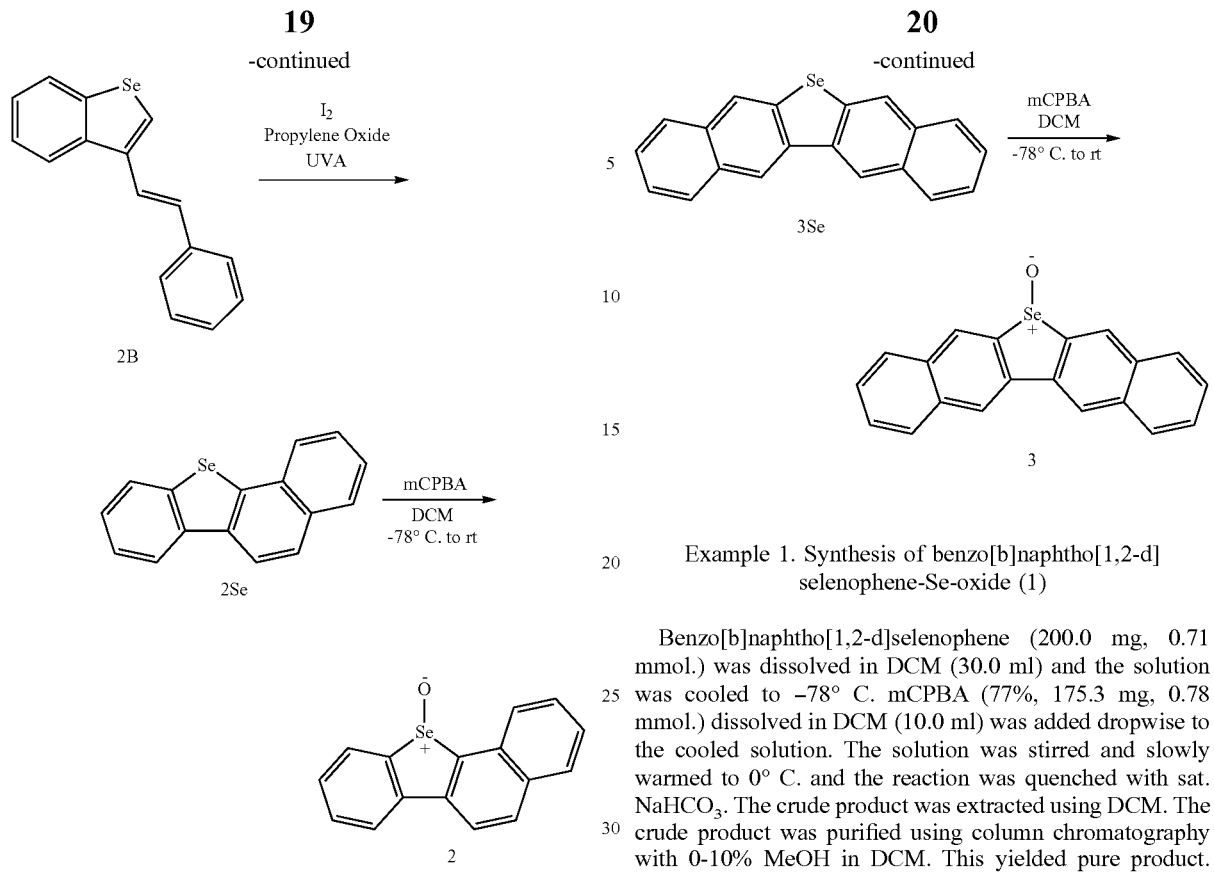

Selenoxide 3 was prepared by slightly modifying the reported synthetic procedure. The modified procedure is shown in Scheme 3. The synthesis of selenide 3Se yielded approximately 90% selenide 3Se and 10% of an isomer, which had the same molecular mass as 3Se. After purification using column chromatography, recrystallization of 3Se in 17% DCM in hexanes eliminated the unidentified isomer. However, the isolated yield after recrystallization was low (10%). Therefore, to prepare selenoxide 3, selenide 3Se containing 10% isomer, or less, was used. Selenoxide 3 prepared by oxidation of 3Se using mCPBA had less than 10% isomer.

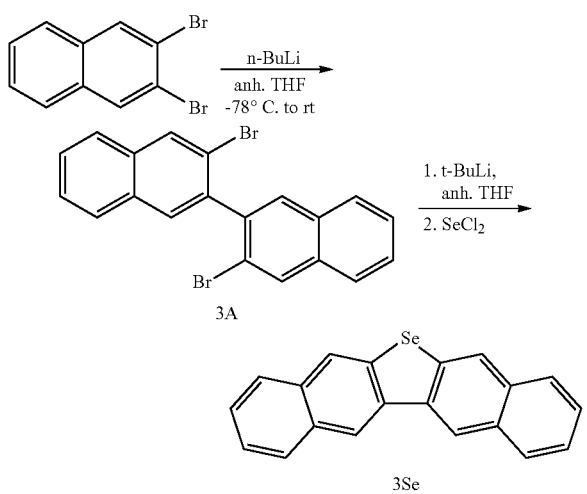

Example 1. Synthesis of benzo[b]naphtho[1,2-d]selenophene-Se-oxide (1)

Benzo[b]naphtho[1,2-d]selenophene (200.0 mg, 0.71 mmol.) was dissolved in DCM (30.0 ml) and the solution was cooled to −78° C. mCPBA (77%, 175.3 mg, 0.78 mmol.) dissolved in DCM (10.0 ml) was added dropwise to the cooled solution. The solution was stirred and slowly warmed to 0° C. and the reaction was quenched with sat. $NaHCO_3$. The crude product was extracted using DCM. The crude product was purified using column chromatography with 0-10% MeOH in DCM. This yielded pure product. (120.6 mg, 57.1%). 1H NMR ($CDCl_3$, 400 MHz, ppm) δ 8.85 (d, J=8.6 Hz, 1H), 8.56 (d, J=8.0 Hz, 1H), 8.05-8.00 (m, 4H), 7.77-7.65 (m, 3H), 7.55 (td, J1=7.5 Hz, J2=0.8 Hz, 1H). 13C NMR ($CDCl_3$, 100 MHz, ppm) δ 146.6, 145.2, 142.4, 136.9, 136.4, 132.7, 131.4, 130.6, 130.1, 129.7, 129.4, 128.6, 129.0, 127.4, 124.5, 124.1. HRMS (ESI/FTICR) m/z: [M+Na]+ Calcd for C16H10OSeNa+ 320.9789; Found 320.9792.

Example 2. Synthesis of 3-bromobenzo[b]selenophene (2A)

$SeO_2$ (11.0 gm, 0.1 mol.) was dissolved in 48% aq. HBr (43.0 ml, 0.4 mol.) and the solution was stirred for 15 min. Phenylacetylene (5 gm, 0.05 mol.) dissolved in a mixture of 2-cyclohexenone (4.7 ml) and dioxane (300.0 ml) was added to $SeO_2$/HBr solution dropwise. The reaction mixture was stirred overnight. DI water was added to quench the reaction. The crude product was extracted using ethyl acetate. The organic phase was dried with anh. $MgSO_4$ and concentrated under reduced pressure. The crude product was purified using column chromatography with hexanes as solvent. This yielded 70% pure product (6.6 gm). GCMS (EI): m/z=260.

Example 3. Synthesis of 3-(2-phenylethenyl)-benzo[b]selenophene (2B)

3-bromo-benzoselenophene (70%, 6.6 gm, 17.8 mmol.), phenyl vinyl boronic acid (3000.0 mg, 20.3 mmol.), SPhos (586.0 mg, 1.4 mmol.), $Na_2CO_3$ (7560.0 mg, 72.0 mmol.), $H_2O$ (45.0 ml), DME (400.0 ml) and methanol (45.0 ml) were added to a round bottom flask equipped with a condenser. The solution was degassed with nitrogen for 30 min and $Pd(PPh_3)_4$ was added. The reaction mixture was refluxed under nitrogen overnight. The solvent was removed under reduced pressure and the crude product was purified using column chromatography with hexanes as solvent and recrystallized in hexanes. This yield white solid (2338.7 mg, 46.5%). $^1$H NMR (CDCl$_3$, 400 MHz, ppm) δ 8.12 (s, 1H), 7.99-7.94 (m, 2H), 7.58 (d, J=7.3 Hz, 2H), 7.48-7.44 (m, 1H), 7.42-7.29 (m, 5H), 7.17 (d, J=16.2 Hz, 1H). $^{13}$C NMR (CDCl$_3$, 100 MHz, ppm) δ 142.0, 140.5, 137.7, 137.6, 131.0, 129.0, 128.0, 126.7, 126.3, 125.0, 124.8, 124.4, 123.9, 122.2. HRMS (ESI/FTICR) m/z: [M+Na]$^+$ Calcd for C$_{16}$H$_{12}$SeNa+ 285.0177; Found 285.0179.

Example 4. Synthesis of benzo[b]naphtho[2,1-d]selenophene (2Se)

3-(2-phenylethenyl)-benzo[b]selenophene (500.0 mg, 1.8 mmol.), Iodine (530.0 mg, 2.1 mmol.), propylene oxide (1.5 ml) and hexanes (500.0 ml) were added to a quartz flask. The solution was degassed with Argon for 30 min and irradiated overnight with UVA bulbs centered at 350 nm. The excess iodine was quenched using sat. NaS$_2$O$_3$ solution. The crude product was extracted using ethyl acetate. The solvent was removed under reduced pressure and the crude product was purified using column chromatography with hexanes as solvent. This yielded white solid (272.6 mg, 54.9%). $^1$H NMR (CDCl$_3$, 400 MHz, ppm) δ 8.21 (d, J=7.4 Hz, 1H), 8.16 (d, J=8.6 Hz, 1H), 8.01-7.96 (m, 3H), 7.90 (d, J=8.6 Hz, 1H), 7.63-7.51 (m, 3H), 7.43 (m, 1H). $^{13}$C NMR (CDCl$_3$, 100 MHz, ppm) δ 139.6, 139.5, 139.5, 135.7, 132.6, 131.5, 129.1, 127.1, 126.6, 126.6, 126.5, 126.3, 126.2, 125.2, 123.3, 121.0. HRMS (ESI/FTICR) m/z: [M+Na]$^+$ Calcd for (C$_{16}$H$_{10}$Se)$_2$Na$^+$ 588.9944; Found 588.9948.

Example 5. Synthesis of benzo[b]naphtho[2,1-d]selenophene-Se-oxide (2)

Benzo[b]naphtho[2,1-d]selenophene (10.0 mg, 0.035 mmol.) was dissolved in DCM (3.0 ml). The solution was cooled to −78° C. mCPBA (77%, 6.7 mg, 0.039 mmol.) dissolved in DCM (1.0 ml) was added and stirred. The solution was slowly warmed to 0° C. and the reaction was quenched with sat. NaHCO$_3$ solution. The crude product was extracted using DCM and the organic phase was dried with anh. MgSO$_4$. The solvent was removed under reduced pressure. The crude product was purified using 0-5% methanol in DCM. This yielded white solid (10.2 mg, 97.8%). $^1$H NMR (DMSO-d$_6$, 400 MHz, ppm) δ 8.29-8.19 (m, 4H), 8.13 (t, J=7.7 Hz, 2H), 7.77-7.65 (m, 3H), 7.57 (t, J=7.5 Hz, 1H). $^{13}$C NMR (DMSO-d$_6$, 100 MHz, ppm) δ 147.0, 144.2, 141.2, 139.0, 133.5, 132.8, 132.1, 130.6, 129.7, 129.1, 129.0, 128.6, 127.3, 125.0, 123.9, 120.6. HRMS (ESI/FTICR) m/z: [M+Na]$^+$ Calcd for C$_{16}$H$_{10}$OSeNa$^+$ 320.9789. Found 320.9791.

Example 6. Synthesis of dinaphtho[2,3-b:2',3'-d]selenophene-Se-oxide (3)

Dinaphtho[2,3-b:2',3'-d]selenophene (100.0 mg, 0.3 mmol.) was dissolved in DCM (15.0 ml). The solution was cooled to −78° C. and mCPBA (77%, 75.0 mg, 0.33 mmol.) dissolved in DCM (5.0 ml) was added dropwise and stirred. The reaction mixture was slowly warmed to room temperature and quenched with sat. NaHCO$_3$. The product was extracted with DCM and the organic phase was dried with anh. MgSO$_4$. The dried organic phase was concentrated under reduced pressure. The crude product was purified using column chromatography with 0-5% methanol in DCM. This yielded yellow solid (40.8 mg, 38.9%). $^1$H NMR (CDCl$_3$, 400 MHz, ppm) δ 8.50 (s, 2H), 8.46 (s, 2H), 8.01-7.96 (m, 4H), 7.67-7.59 (m, 4H), 7.67-7.59 (m, 4H). $^{13}$C NMR (CDCl$_3$, 100 MHz, ppm) δ 143.3, 137.3, 135.4, 134.0, 130.5, 129.2, 129.0, 128.9, 127.8, 122.6. HRMS (ESI/FTICR) m/z: [M+Na]$^+$ Calcd for C$_{20}$H$_{10}$OSeNa$^+$ 370.9946; Found 370.9948.

Example 7. Synthesis of perylo[1,12-bcd]selenophene-Se-oxide (4)

Perylo[1,12-bcd]thiophene (56.3 mg, 0.17 mmol.) was dissolved in DCM (40.0 ml). The solution was cooled to −78° C. and mCPBA (77%, 42.0 mg, 0.19 mmol.) dissolved in DCM (10.0 ml) was added. The solution was stirred and warmed to room temperature and quenched with sat. NaHCO$_3$ solution. The product was extracted using DCM. The organic phase was concentrated under reduced pressure. The crude product was purified using column chromatography with 0-5% methanol in DCM. This yielded reddish yellow solid (36.5 mg, 61.8%). $^1$H NMR (DMSO-d$_6$, 400 MHz, ppm) δ 8.40 (d, J=7.4 Hz, 2H), 8.02 (d, J=8.5 Hz, 2H), 7.91 (d, J=1.7 Hz, 2H), 7.88 (d, J=2.1 Hz, 2H), 7.68 (t, J=7.9 Hz, 2H). $^{13}$C NMR (Acetic acid-d$_4$, 100 MHz, ppm) δ 137.4, 133.6, 132.5, 131.7, 128.1, 127.4, 127.2, 126.7, 125.4, 121.4. HRMS (ESI/FTICR) m/z: [M+Na]$^+$ Calcd for C$_{20}$H$_{10}$OSeNa+368.9789; Found 368.9793.

Example 8

Figure 1B:
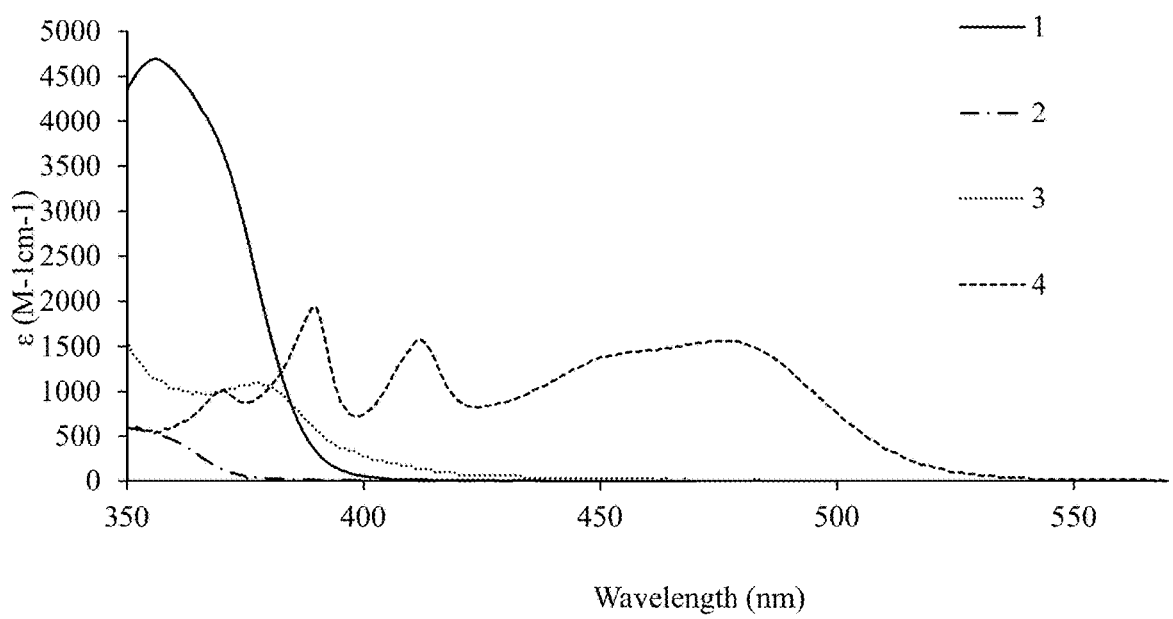
FIG. 1B is a plot of the extinction coefficient ($M^{-1}cm^{-1}$) at different wavelengths for DBSeO and compounds 1-4.

The UV-Vis spectra of compounds 1-4 were obtained to determine if visible light was absorbed by compounds 1-4. Compounds 1-4 had cutoff wavelengths (F<50) that are significantly higher than DBTO (356 nm) and DBSeO (352 nm). Compounds 1 and 2 had cutoff wavelengths of 400 nm and 376 nm respectively and selenoxides 3 and 4 absorption extend above 400 nm, with cutoff wavelengths of 433 nm and 533 nm, respectively (see FIG. 1A and FIG. 1B).

Example 9. Determination of Quantum Yield of Photodeoxygenation

Photodeoxygenation of DBTO is the commonly used clean source of O($^3$P) in the condensed phase. However, it suffers from low quantum yield of photodeoxygenation. The selenoxides 1-4 were synthesized to improve the quantum yield of photodeoxygenation and therefore make the generation of O($^3$P) more efficient. To verify whether 1-4 undergo photodeoxygenation more efficiently, the quantum yields of photodeoxygenation of compounds 1-4 were measured upon UV irradiation. These experiments were performed in ethanol and acetonitrile.

1-5 mM solutions of compounds 1-4 were prepared in HPLC grade acetonitrile. The optical densities of the prepared solutions were ensured to be greater than 2 at the desired wavelength for photolysis. 4.0 ml of prepared samples in quartz cuvettes (1 cm×1 cm) cells with long stem were degassed with argon for 10 min. The degassed solutions in quartz cuvettes were irradiated using a 75 W Xenon lamp focused on a monochromator (Photon Technologies International). The reactions were carried out to low conversions (<20%). HPLC was used to analyze the solutions before and after photolysis. Photorearrangement of azoxybenzene to 2-hydroxyazobenzene was used as an actinometer for wavelengths less than 390 nm and for wavelengths above 390 nm, K[Cr(NH$_3$)$_2$(NCS)$_4$] was used.

These experiments were performed in ethanol and acetonitrile. For individual selenoxides, the wavelength with maximum absorbance above 320 nm in the UV-Vis spectrum was used for irradiation. The quantum yields of photodeoxygenation were calculated based on the increase in the selenide concentration and are listed in Table 1. The values ranged from 0.009 to 0.33. Among the compounds tested, selenoxide 2 had the highest quantum yield of photodeoxygenation which was 0.33 and selenoxide 4 had the lowest quantum yield of 0.009. The quantum yield of photodeoxygenation of compound 4 was only obtained in ethanol as it was not soluble in acetonitrile. Photolysis of 2 upon UVA irradiation yielded corresponding selenide 2Se and a new compound 2X. $^1$H NMR of compound 2X, which is included in the supporting information, had peaks with chemical shifts in the aromatic region and resembled a polymer. For calculating the quantum yield of photodeoxygenation, HPLC analysis was used to determine the increase in the selenide concentration. No other significant products were observed in HPLC analysis after photolysis of 1-4 other than their corresponding selenides. This is surprising as photodeoxygenation of DBSeO yields DBSe and a ring expanded selenic ester product. To measure the light flux of the lamp used, photorearrangement of azoxybenzene to 2-hydroxyazobenzene was used as the actinometer.

TABLE 1

Quantum yields of Photodeoxygenation of compounds DBSeO, 1-4

| Compound | Quantum Yield[b] $\Phi_{+selenide}$ | | Wavelength (nm) |
|---|---|---|---|
| | Acetonitrile | Ethanol | |
| DBSeO | — | 0.13 ± 0.01[a] | 320 ± 12 |
| 1 | 0.14 ± 0.03 | 0.21 ± 0.01 | 356 ± 6 |
| 2 | 0.25 ± 0.01 | 0.33 ± 0.15 | 340 ± 6 |
| 3 | 0.23 ± 0.04 | 0.19 ± 0.02 | 330 ± 6 |
| 4 | — | 0.009 ± 0.006 | 320 ± 6 |

[a]Quantum yield of photodeoxygenation of DBSeO from ref. 16.
[b]Quantum yields reported are within 95% confidence intervals and were calculated by increase in selenide concentration.

Examples 10. Photochemistry of 1-3 with UVA Irradiation

Examples 11-14 explore the photochemistry of compounds 1-4 with UVA irradiation by measuring their oxidizing effects on various substrates. A number of substrates such as toluene, benzene, styrene and 1-octene have been oxidized using O($^3$P) produced by the photodeoxygenation of DBTO. These substrates yield multiple products upon reaction with O($^3$P). For instance, oxidation of toluene by O($^3$P) yields benzyl alcohol, o-cresol, m-cresol and p-cresol in a specific ratio. Two different chemical reactions can be shown to share a common intermediate if the reactions yield the same product distribution. Therefore, if the oxidation of substrates by the photodeoxygenation of 1-4 produces the same distribution of products as DBTO, then 1-4 are considered to produce O($^3$P) on photodeoxygenation. Three different common intermediate experiments were conducted to verify if selenoxides 1-4 produce O($^3$P) on photodeoxygenation. Toluene, benzene and 1-octene were used as substrates in these common intermediate experiments for 1-3. Since compound 4 is not soluble in toluene or benzene, oxidation of toluene or benzene common intermediate experiments were not conducted for 4. However, the 1-octene common intermediate experiment of 4 was performed in ethanol as the solubility of 4 in acetonitrile was very low.

Example 11. General Procedure for Intermediate Experiments 1-10 mM solutions of DBTO, compounds 1-4 were prepared (For benzene test at low concentration approx. 0.2 mM was used). The solutions were degassed with Argon in quartz cuvettes (1 cm×1 cm) with long stems. The degassed solutions were irradiated with UVA bulbs (LCZ-UVA bulbs centered at 350 nm). The change in the concentrations of products were analyzed using GC-FID and change in the concentration of DBT and corresponding selenides of 1-4 were analyzed using HPLC. Dodecane was used as internal standard.

Example 12. Oxidation of Toluene Common Intermediate Experiment for DBTO, DBSeO, and 1-3

The oxidation of toluene has been used as a common intermediate experiment to verify if the oxidant formed during the photodeoxygenation of sulfoxides and selenoxides is the same and likely O($^3$P). However, the results must be carefully analyzed since the ratio of the oxidized products is sensitive to the amount of dissolved molecular oxygen. This sensitivity arises from the ability of dissolved molecular oxygen to oxidize toluene upon UVA irradiation. Irradiation of toluene for 4 hours, which was degassed using argon sparging, with UVA light yielded mainly benzaldehyde and benzyl alcohol and some cresols in a 10:1 CH$_3$:Ring ratio of oxidation products. As shown in the reaction below, when toluene was degassed by argon sparging, the oxidation of toluene by the photodeoxygenation of DBTO yielded 1:3 CH$_3$:Ring ratio (Table 2, entry 1) upon 4 hours of UVA irradiation. However, when the freeze pump thaw technique, which is a superior technique for removing dissolved oxygen, was used to degas toluene, the amount of benzaldehyde obtained was negligible and the ratio of CH$_3$:Ring obtained was 1:17 (Table 2, entry 2). It should also be noted the head space for all of the argon sparged samples was the same, which has been shown to effect the ratio of oxidized products.

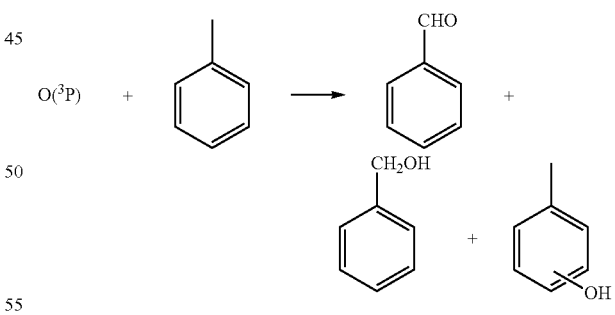

Unlike DBTO, the CH$_3$:Ring ratio obtained for the oxidation of toluene by photodeoxygenation of DBSeO was 1:26 (Table 2, entry 3) when degassed by argon sparging. This was due to the higher quantum yield of photodeoxygenation of DBSeO compared to DBTO, which results in a difference in the photolysis time of DBTO and DBSeO. When 14 Luzchem UVA bulbs (LZC-UVA) were used for irradiation, the photolysis time for DBTO was 4 hours to yield approximately 0.5 mM DBT whereas DBSeO was photolyzed for only 10 minutes to yield approximately 0.5 mM DBSe. Thus, the longer irradiation time for DBTO affected the CH₃:Ring ratio for argon sparged samples due to the background oxidation of toluene by the residual dissolved molecular oxygen. The product ratio obtained for DBSeO when degassed using argon sparging was similar to the product ratio obtained for DBTO when freeze-pump-thaw technique was used to remove oxygen. Therefore, as the quantum yields of photodeoxygenation of selenoxides 1-3 are closer to DBSeO, argon sparging was used to degas the photolysis samples. The ratio obtained for DBSeO was considered as the reference ratio.

Oxidation of toluene by the photodeoxygenation of DBTO, DBSeO and 1-3 produced more cresols than benzaldehyde and benzyl alcohol after photolysis. No other toluene oxidation products for DBTO, DBSeO and 1-3 were observed in GC-FID analysis after photolysis. The product yields of DBSeO and 1-3 were calculated relative to the formation of selenide. For DBTO, the product yields were calculated relative to the formation of DBT. HPLC analysis was used to determine the increase in the selenide and DBT concentration. The photolysis time for 1-3 and DBSeO was approximately 10 minutes, while for DBTO it was 4 hours. The total product yields obtained for DBTO when toluene was degassed by argon sparging and freeze pump thaw were 42±4% and 33±5%, respectively. The total product yield obtained for DBSeO was 32±7% which is within the limits of the experimental error of the yields obtained for DBTO. Compound 1 had a similar CH₃:Ring oxidation ratio of 1:27 compared to DBSeO. The total product yield obtained for 1 was 17±4%, which is lower than the total product yield obtained for DBSeO. Similar to 1, compound 2 had 1:25 CH₃: Ring oxidation, which is similar to DBSeO. However, the total product yield obtained for 2, 18±0.9%, is also lower than that of DBSeO. For selenoxide 3, the CH₃:Ring oxidation ratio obtained was 1:11, which is slightly lower than DBSeO in terms of amount of ring oxidation. However, the CH₃:Ring oxidation ratio can be considered as nearly 0:1 because the errors obtained for the yields of benzaldehyde and benzyl alcohol are high. Although these results suggest that compounds 1-3 produce the same oxidant as DBTO and DBSeO, namely O($^3$P), the oxygen sensitivity makes the oxidation of toluene a less robust approach to make this conclusion.

O($^3$P) is the intermediate of photodeoxygenation of sulfoxides and selenoxides. Benzene when oxidized by O($^3$P) predominantly produces phenol along with biphenyl as shown in the reaction below. The product distribution of this test is not oxygen sensitive since irradiation of benzene with UVA did not yield any benzene oxidation products even when the solution was not degassed. Hence, the product distribution of the oxidation of benzene should not be affected due to a difference in irradiation times.

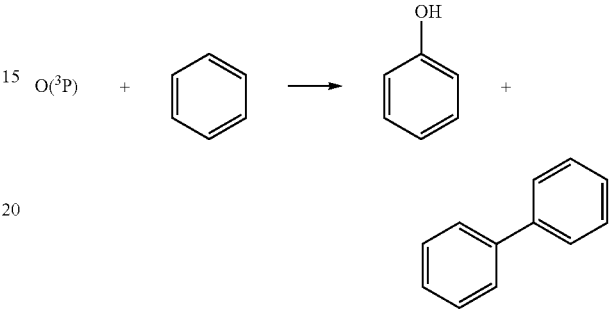

Oxidation of benzene as a common intermediate experiment was conducted for DBTO, DBSeO, and 1-3. The photolysis time for 1, 2 and DBSeO was 3 minutes and for DBTO and 3 were 60 minutes and 5 minutes respectively. The product distribution and total product yields of DBTO, DBSeO, and 1-3 are listed in Table 3. Photolysis of DBTO, DBSeO, and 1-3 primarily yielded phenol with biphenyl as the minor product. No other benzene oxidation products were observed in GC-FID analysis after photolysis. Compounds 1-3 had similar product distribution as obtained for DBSeO and DBTO, but the total product yields obtained were lower. For compound 1, the total product yield obtained, 18.4±0.1%, is lower than the total product yield obtained for DBSeO (32±6%) and DBTO (33±2%). Similar to 1, the total product yield of 2, 17.9±0.9% was lower compared to DBTO and DBSeO. Compound 3 had the

TABLE 2

Product distribution and yields of toluene oxidation by photolysis of DBTO, DBSeO and 1-3

| | Percentage Product Yield (%)[a] | | | | Total | |
|---|---|---|---|---|---|---|
| Compound | Benzaldehyde | Benzyl alcohol | o-Cresol | m/p-Cresol[b] | Product Yield (%) | CH₃:Ring[c] |
| DBTO[d] | 5 ± 3 | 6 ± 3 | 17.6 ± 0.9 | 13 ± 1 | 42 ± 4 | 1:3 |
| DBSeO | 1.2 ± 0.2 | 0.0 ± 0.2 | 18 ± 3 | 13 ± 3 | 32 ± 7 | 1:26 |
| 1 | 0.2 ± 0.2 | 0.4 ± 0.1 | 9 ± 3 | 7 ± 1 | 17 ± 4 | 1:27 |
| 2 | 0.5 ± 0.9 | 0.2 ± 0.4 | 11.6 ± 0.5 | 6.1 ± 0.1 | 18.4 ± 0.9 | 1:25 |
| 3 | 2 ± 2 | 0.2 ± 0.9 | 7 ± 3 | 4 ± 2 | 13 ± 7 | 1:5 |

[a]Percentage product yields are calculated with respective to formation of selenide and are within 95% CI.
[b]Calculated as one peak.
[c]Ratio of sum of yields of PhCHO and benzyl alcohol to combined yields of cresols.
[d]

Example 13. Oxidation of Benzene Common Intermediate Experiment for DBTO, DBSeO As oxidation of toluene common intermediate experiment is oxygen sensitive, other common intermediate experiments have been explore. Oxidation of benzene is another common intermediate experiment that has been used to confirm if lowest total product yield of 7.7±0.2% compared to all the other entries in Table 3. The similar product ratio implies that 1-3 produce O($^3$P) upon photodeoxygenation. However, as the total product yields of 1-3 are lower than the total product yields of DBSeO and DBTO, 1-3 might also undergo photodeoxygenation through an alternate pathway which does not result in the oxidation of benzene.

TABLE 3

Product distribution and yields of benzene oxidation by photolysis of DBTO, DBSeO and 1-3

| Compound | Percentage Product Yields (%)[a] Phenol | Biphenyl | Total Product Yield (%) |
|---|---|---|---|
| DBTO | 32 ± 2 | 1.0 ± 0.1 | 33 ± 2 |
| DBSeO | 31 ± 6 | 0.8 ± 0.5 | 32 ± 6 |
| 1 | 17.40 ± 0.03 | 1.0 ± 0.1 | 18.4 ± 0.1 |
| 2 | 17.5 ± 0.7 | 0.40 ± 0.01 | 17.9 ± 0.9 |
| 3 | 7.4 ± 0.2 | 0.30 ± 0.01 | 7.7 ± 0.2 |

[a]Percentage product yields are calculated with respective to formation of selenide and are within 95% CI.

Example 14. Oxidation of 1-octene Common Intermediate Experiment

Oxidation of 1-octene common intermediate experiment was performed to confirm that photodeoxygenation of 1-3 produce O($^3$P). The reaction of 1-octene and O($^3$P) gives 1,2-epoxyoctane and 1-octanal as products as shown below.

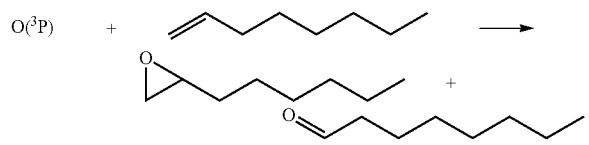

Similar to oxidation of benzene common intermediate experiment, the product distribution of this common intermediate experiment is not oxygen sensitive as no 1-octene oxidation products were obtained by the irradiation with UVA of 1-octene (500 mM) in acetonitrile when the solution was not degassed. The details of 1-octene oxidation test are listed in Table 4.

TABLE 4

Product distribution and yields of 1-octene oxidation by photolysis of DBTO, DBSeO and 1-3

| Compound | Product Yields[a] 1-octanal (%) | 1,2-epoxyoctane (%) | Total Product Yield | 1-octanal:1,2-epoxy octane[b] |
|---|---|---|---|---|
| DBTO | 24 ± 2 | 35 ± 3 | 59 ± 6 | 1:1.4 |
| DBSeO | 11.0 ± 0.2 | 14.4 ± 0.9 | 25.4 ± 0.7 | 1:1.3 |
| 1 | 5.9 ± 0.4 | 7.00 ± 0.04 | 13.0 ± 0.3 | 1:1.2 |
| 2 | 3.4 ± 0.6 | 4.9 ± 0.5 | 8 ± 1 | 1:1.4 |
| 3 | 5 ± 1 | 7 ± 2 | 11 ± 3 | 1:1.3 |

[a]Percentage product yields are calculated with respective to formation of selenide and are within 95% CI.
[b]Ratio of yield of 1-octanal to yield of 1,2-epoxyoctane Compounds 1-3 along with DBTO and DBSeO were used to oxidize 1-octene in acetonitrile. The photolysis time for DBTO was approximately 4 hours and for DBSeO and 1-3 was approximately 5 minutes. The results of the 1-octene oxidation test are listed in Table 4. The product distributions obtained for DBTO, DBSeO, and 1-3 were alike. The ratios of 1-octanal to 1,2-epoxyoctane obtained for DBTO, DBSeO, and 1-3 were around 1:1.3. The total product yield obtained for DBTO was 59±6% which is significantly higher than the total product yield of DBSeO which was 25±0.7%. Compound 1 had a total product yield of 13±0.3% which is lower than both DBTO (59±6%) and DBSeO (25±0.7%).

The total product yields of 2 and 3 are 8±1% and 11±3% respectively. Again, the similar product ratio suggests that compounds 1-3 generate O($^3$P) upon irradiation like DBTO. However, the lower yields for 1-3, which were also observed in the tests with toluene and benzene, suggests other deoxygenation mechanisms that do not produce O($^3$P) could be operative.

Example 15. Oxidation of 1-Octene of 4 in Ethanol

Common intermediate experiments for 4 were not possible due to low solubility in acetonitrile, which is required to obtain significant oxidation of toluene or benzene. However, the oxidation of 1-octene as a common intermediate experiment could be performed in ethanol. Since ethanol is more reactive with O($^3$P) than acetonitrile, a lower yield of 1-octanol and 1,2-epoxyoctane was expected. When DBSeO was irradiated in ethanol with 500 mM 1-octene, the total product yield of 1-octanal and 1,2-epoxyoctane dropped to 4%. Irradiation of 4 in ethanol with 500 mM 1-octene with UVA light resulted in 4Se; however, GC-FID analysis showed neither a 1-octanal nor a 1,2-epoxyoctane peak. Given the detection limit of 1-octanal and 1,2-epoxyoctane, 4 produces at least 2 times less O($^3$P) than DBSeO or possibly none at all. The concentrations of DBSeO and 4 in ethanol used for 1-octene oxidation were both 1.1 mM.

The total product yields obtained for DBTO and DBSeO in the oxidation of toluene and oxidation of benzene common intermediate experiments were similar. However, the total product yield obtained for DBSeO for the 1-octene oxidation common intermediate experiment was much lower than the total product yield obtained for DBTO. To examine if solvent effects influenced these oxidations, DBTO and DBSeO were photolyzed individually with 1-octene in dichloromethane. No significant change in the total product yields was observed when the solvent was changed to dichloromethane from acetonitrile for both DBTO and DBSeO. The total product yields of oxidation of 1-octene by photodeoxygenation of DBTO and DBSeO in dichloromethane were 70±8% and 29±3%. Therefore, the lower total product yield for DBSeO was not due to different solvent effects for DBSeO and DBTO. A similar observation was reported previously when a mixture of benzene and cyclohexane, in the ratio of 3:1 (v/v), was oxidized in dichloromethane individually by photolysis of DBTO and DBSeO. Both DBTO and DBSeO yielded product ratios which were approximately 1:3 phenol:cyclohexanol. However, the total product obtained for DBSeO, 6.2±0.8%, was significantly lower compared to the total product yield, 42±5.1%, obtained for DBTO. The reason for the lower product yields of 1-octene oxidation by DBSeO compared to DBTO was not investigated.

Example 16. Summary of Common Intermediate Experiments

The results of the three common intermediate experiments suggest that photodeoxygenation of selenoxides 1-3, DBSeO and DBTO have O($^3$P) as a common intermediate. The product ratios for all the three common intermediate experiments of selenoxides 1 and 2 were similar to the reference ratios. However, the total product yields of 1 and 2 were lower than to that of DBTO and DBSeO. Selenoxide 3 had a different product ratio compared to the reference in the case of oxidation of toluene common intermediate experiment but have product ratios similar to the reference for oxidation of benzene and 1-octene common intermediate experiments.

The common intermediate experiments proved that photodeoxygenation of selenoxides 1-3 yield O($^3$P). However, it is unclear why the total product yields of the common intermediate experiments were lower than DBTO and DBSeO. One explanation is that 1-3 photodeoxygenate through an additional pathway which does not produce O($^3$P). To understand this phenomenon, mechanistic studies for 1-3 were conducted. Selenoxides 1-3 were individually dissolved in EPA glass (ether:pentane:ethyl alcohol=5:5:2) and photolyzed at 77 K by UVA irradiation. HPLC analysis after the photolysis showed increase in the corresponding selenide concentration. Although, this indicates a unimolecular mechanism for photodeoxygenation of 1-3, it does not rule out additional bimolecular photoreduction mechanism.

Example 17. Bimolecular Photoreduction Mechanisms

The potential for a bimolecular exciplex was tested for selenoxide 1. Direct irradiation of selenoxide 1 dissolved in acetonitrile with 390±3 nm light in presence of DBSeO yielded 1Se and DBSe. The UV-Vis cut off wavelength of DBSeO is 352 nm. Thus, the observed deoxygenation of both DBSeO and 1 in these conditions implied either a bimolecular exciplex, or energy transfer from excited 1 to DBSeO, which both would be expected to result in 1Se and DBSe. To differentiate them, selenoxide 1 was irradiated with 390±3 nm light at variable concentrations of DBSeO and 500 mM of 1-octene. Acetonitrile was used as the solvent for these experiments, and the results of these experiments are shown in the Table 5.

TABLE 5

Product distribution and yields of 1-octene oxidation by direct irradiation of 1 in presence of DBSeO

| Initial Concentration (mM) | | Total Product Yield$^a$ | 1-octanal:1,2-epoxy octane$^b$ |
| --- | --- | --- | --- |
| Selenoxide 1 | DBSeO | | |
| 1.7 | 0.0 | 15 ± 2 | 1:1.5 |
| 1.7 | 0.4 | 13 ± 2 | 1:1.4 |
| 1.7 | 0.8 | 14 ± 2 | 1:1.4 |
| 1.7 | 1.6 | 11.1 ± 0.1 | 1:1.4 |
| 1.7 | 3.2 | 12 ± 2 | 1:1.4 |

$^a$Percentage product yields are calculated with respective to formation of 1Se and DBSe. The values are within 95% CI.
$^b$Ratio of yield of 1-octanal to yield of 1,2-epoxyoctane The product ratio 1-octanal: 1,2-epoxyoctane was approximately 1:1.4 for all the experiments. The total product yields for all the experiments were within the limits of the experimental error. If there was any bimolecular photoreduction, the total product yields should decrease with increase in the concentration of DBSeO. Therefore, photodeoxygenation of DBSeO by direct irradiation of 1 occurred by energy transfer from the excited state of 1 rather than through a bimolecular exciplex that dissociates to deoxygenated products.

Direct irradiation of 1 in methanol with 390±3 nm in presence of diphenyl selenoxide was performed to provide more evidence that 1 does not undergo deoxygenation through a bimolecular exciplex. As selenoxide 1 and diphenyl selenoxide had higher solubility in methanol compared to acetonitrile, methanol was used for this reaction. This reaction did not yield any diphenyl selenide after the reaction. Similarly, direct irradiation of 2 and 3 individually in methanol in presence of diphenyl selenoxide did not yield any diphenyl selenide for either reaction. The wavelengths used for irradiation of 2 and 3 were 350±3 nm and 390±3 nm, respectively.

As a bimolecular exciplex was ruled out, another possible mechanism that was investigated was electron transfer. As the selenides 1Se-3Se are produced during the photodeoxygenation of 1-3, photoinduced electron transfer from the selenide to the selenoxide could result in deoxygenation without the release of O($^3$P). This hypothesis was tested by obtaining the total product yields of 1-octene oxidation by photodeoxygenation of 2 at different reaction time points. The total product yields of 1-octene oxidation at all the reaction time points were in the range of 8±4% which is similar to the total product yield reported in table 4. In another experiment, 2Se was added to the solution containing 2, 1-octene, and acetonitrile. The concentrations of 2 and 2Se were both 2 mM. This solution was irradiated, and the total yield of the 1-octene oxidation products was obtained. The obtained total oxidation product yield was in the same range as reported in Table 4. These results indicate no electron transfer from 2Se to 2 during the photolysis process. Similar results were expected for 1 and 3.

The possibility of a unimolecular mechanism that does not produce O($^3$P), which would result in lower total product yields, was investigated. Photodeoxygenation of DBTO to DBT and O($^3$P) occurs from the $T_2$ triplet state of DBTO. However, the $T_1$ state of DBTO accessed by triplet sensitization was shown to cause photodeoxygenation to produce DBT, but this process does not yield O($^3$P). In contrast, photodeoxygenation of DBSeO occurs through both $T_1$ and $T_2$ triplet states to produce DBSe and O($^3$P). The total product yields of the common intermediate experiments of 1-3 would be lower if the selenoxides 1-3 deoxygenated through both $T_1$ and $T_2$ but only produced O($^3$P) from the $T_2$ state as with DBTO. Photosensitization of selenoxides 1-3 to the $T_1$ state could be used to test this hypothesis. The energies of $T_1$ triplet states of 1-3 were obtained computationally using a HSEH1PBE/6-311G(d,p) level of theory. The $T_1$ triplet states energies of 1-3 are shown in Table 6.

TABLE 6

Triplet energies of selenoxides 1-3

| Selenoxide | $T_1$ Energy (kcal/mol.) |
|---|---|
| 1 | 46.8 |
| 2 | 39.8 |
| 3 | 49.2 |

Acridine orange was chosen as the sensitizer because its triplet energy of 50.2 kcal/mol was close to the calculated triplet energies of 1-3. Hence, the $T_1$ triplet state of acridine orange has enough energy to promote 1-3 to their corresponding $T_1$ triplet states. However, acridine orange could also act as an electron donor in its excited state as its halfwave oxidation potential is lower compared to aniline, which is a good electron donor. Therefore, both mechanisms have to be considered while using acridine orange to sensitize 1-3.

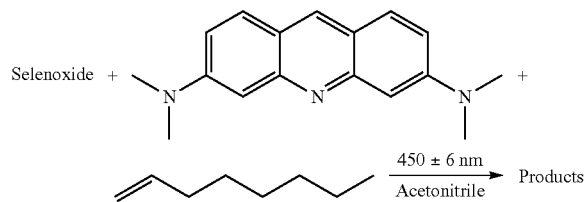

Selenoxides 1-3 dissolved in acetonitrile were excited by sensitization using acridine orange in presence of 1-octene. HPLC analysis after the experiment showed that triplet sensitization resulted in photodeoxygenation of 1 to 1Se. However, GC-FID analysis showed no formation of 1-octene oxidation products. Similarly, sensitization of selenoxide 3 yielded 3Se but no 1-octene oxidation products were obtained. Interestingly, sensitization of 2 produced only 2Se and no 2X, which was the other product obtained when 2 was directly irradiated with UVA light. GC-FID analysis of this reaction showed that 1-octene was oxidized to 1-octanal and 1-octanol. However, as 1,2-epoxyoctane was not obtained, it can be concluded that $O(^3P)$ was not produced during photosensitization of 2.

The photosensitization of 1-3 by acridine orange could have occurred by energy transfer from the $T_1$ triplet state of acridine orange to $T_1$ triplet state of 1-3 or by electron transfer from excited state of acridine orange to the ground state of 1-3 or by both mechanisms. If the deoxygenation of 1-3 occurred through energy transfer, it suggests that $T_1$ triplet state of 1-3 did not produce $O(^3P)$. However, if the deoxygenation occurred by electron transfer, it would lead to reduction of 1-3 to their corresponding selenide and nothing can be concluded about the deoxygenation of 1-3 in their $T_1$ triplet state. To determine if the halfwave oxidation potential of acridine orange made electron transfer feasible, perylene, which has much lower triplet state energy but similar halfwave oxidation potential, was used as the photosensitizer to induce electron transfer. The triplet state energy and half wave oxidation potential of perylene are 36.1 kcal/mol. and 0.85 V vs SCE (Table 7), respectively. Selenoxide 1 was chosen for this experiment as the calculated $T_1$ triplet state energy of 1 was higher than that of perylene and 1 had a UV-Vis cutoff wavelength lower than that of perylene. Therefore, only the electron transfer mechanism is possible in this case. Perylene (1.3 mM) was excited using 435±3 nm in presence of selenoxide 1 (3.8 mM), 1-octene (500 mM) and dodecane (0.125 mM) in acetonitrile. GC-FID and HPLC analyses showed formation of 1Se (0.23 mM) but no 1-octene oxidation products. These results imply that 0.85 V vs SCE halfwave oxidation potential is sufficient for an electron transfer mechanism. However, as the calculated $T_1$ triplet state energy of acridine orange is higher than that of 1-3, energy transfer mechanism cannot be ruled out. Additional studies to selectively perform energy transfer using a photosensitizer to selenoxides 1-3 were not conducted due to limitations in readily available photosensitizers with properties that would facilitate only energy transfer and not electron transfer.

Therefore, deoxygenation of 1-3 by photosensitization using acridine orange could have occurred by an energy transfer mechanism or electron transfer mechanism or by both these mechanisms. Hence, it is inconclusive whether the $T_1$ energy state of 1-3 produces $O(^3P)$. Other photosensitizers with high halfwave oxidation potential could not be used for these experiments, as they had lower UV-Vis cutoff wavelengths than 1-3.

TABLE 7

Halfwave Oxidation Potentials and Triplet state energies of Acridine Orange and Perylene.

| Photosensitizer | $E_{1/2}^{ox}$/V vs SCE in Acetonitrile | $T_1$ Energy (kcal./mol.) |
|---|---|---|
| Acridine Orange | 0.82 | 50.2 |
| Perylene | 0.85 | 36.1 |

All the above mechanistic studies suggest that photodeoxygenation of 1-3 is a unimolecular process and not bimolecular. However, the efforts to identify a photoinduced deoxygenation mechanism that would account for the lower total oxidation product yields observed in the common intermediate experiments were not successful.

Example 18. Photochemistry of 1 and 3 with Visible Light Irradiation

The primary goal of this work was to prepare photoactivatable $O(^3P)$ precursors that generate $O(^3P)$ using visible light irradiation. Therefore, compounds which absorb in visible light, 1 and 3, were tested with a common intermediate experiment. 1-octene was used as the substrate and acetonitrile was used as the solvent. Bulbs centered at 420 nm (Luzchem LZC-420 nm, 14 bulbs) were used for irradiation. The use of glass or quartz test tube had no effect on the observed products or yields. Selenoxides 1 and 3 were photolyzed for 1 hour and 4 hours respectively. The product yields of 1-octene oxidation by the irradiation of 1 at 420 nm light were measured. Upon irradiation, 1 yielded 1,2-epoxyoctane and 1-octanal upon irradiation in a ratio 1:1.2. The total product yield obtained was 13±2%, which was similar to the total product yield of 1-octene oxidation obtained by UVA irradiation of 1. The product ratio is similar to the product ratio of DBSeO listed in Table 5. The product distribution and total product yield of 1 are similar to that of the 1-octene oxidation common intermediate experiment performed by using bulbs centered at 350 nm. The implication of these results is the photodeoxygenation of 1 produces $O(^3P)$ upon irradiation with visible light.

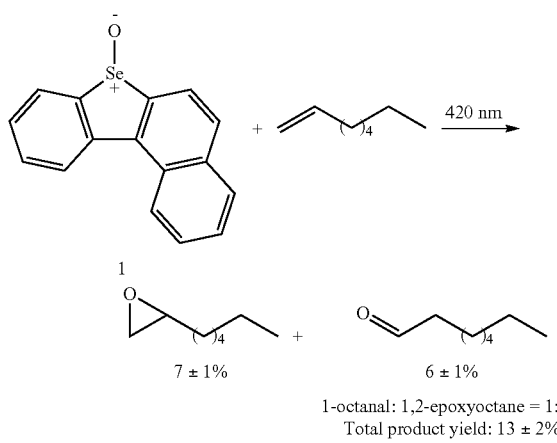

1-octanal: 1,2-epoxyoctane = 1:1.2
Total product yield: 13 ± 2%

Irradiation of 3 with visible light resulted in the photodeoxygenation of 3. However, unlike 1, the oxidation of 1-octene common intermediate test of 3 did not yield any detectable amounts of 1-octanal or 1,2-epoxyoctane. This indicates the photodeoxygenation of 3 induced by visible light irradiation produces considerably less or no O($^3$P) compared to irradiation with UVA light. The reason for this wavelength dependence was not investigated.

Example 19. Determination of Quantum Yield of Photodeoxygenation at 400 nm

The UV-Vis cutoff wavelengths ($_\epsilon$<50) for 1 and 3 are 400 nm and 433 nm. The quantum yields of photodeoxygenation of 1 and 3 are obtained in ethanol at wavelength range 400±3 nm and are listed in Table 8. Saturated solutions of 1 and 3 in ethanol had optical densities greater than 2. K[Cr(NH$_3$)$_2$(NCS)$_4$] was used as the actinometer. The quantum yields of photodeoxygenation of 1 and 3 were 0.13±0.03 and 0.37±0.03 respectively.

TABLE 8

Quantum yields of photodeoxygenation of 1 and 3 at 400 nm

| Compound | Quantum Yield $\Phi_{+selenide}$ [a] | Wavelength (nm) |
|---|---|---|
| 1 | 0.13 ± 0.03 | 400 ± 3 |
| 3 | 0.37 ± 0.03 | 400 ± 3 |

[a] Quantum yields reported are within 95% confidence intervals and calculated based on the increase in selenide concentration. 400 ± 3 nm wavelength light was used for photolysis and ethanol was used as the solvent.

Example 20. Excitation and Emission Spectra of Compound 4

Figure 2:
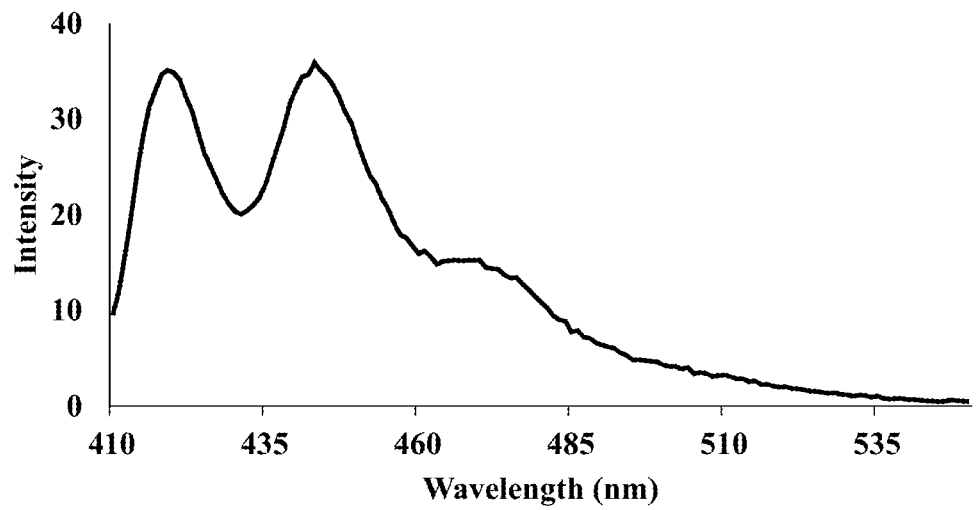
FIG. 2 show emission (Panel A) and excitation (Panel B) spectra of compound 4.
Figure 2:
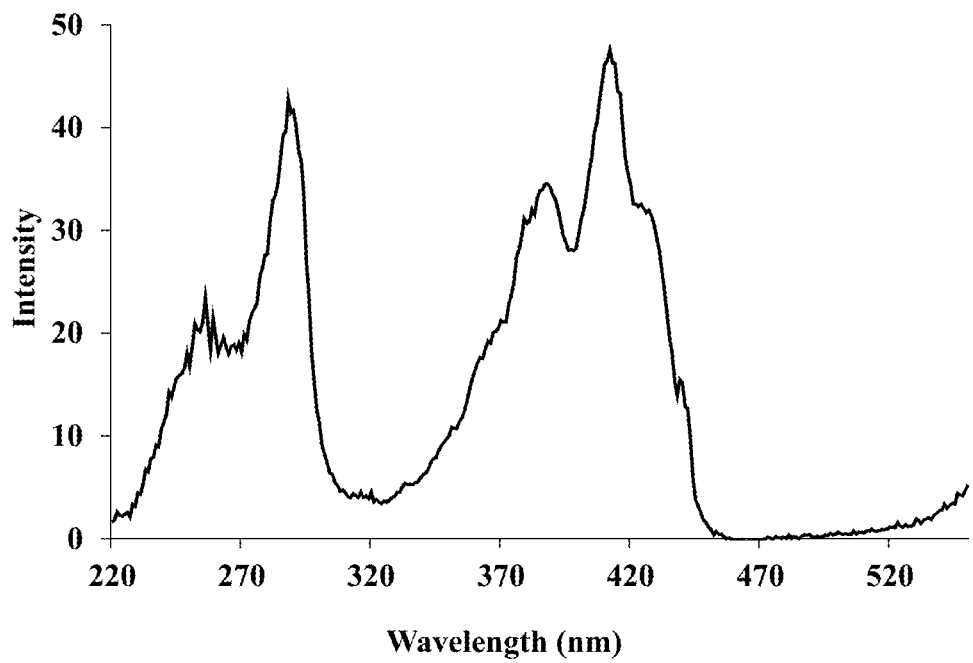

Perylo[1,12-bcd]selenophene Se-oxide (4) was synthesized to test if photodeoxygenation of 4 produces O($^3$P). Photodeoxygenation quantum yield experiments showed that compound 4 photodeoxygenates upon irradiation of 320 nm light. However, the intermediate of photodeoxygenation of 4 could not be characterized as it was not soluble in toluene, benzene and acetonitrile. Compound 4 is unique compared to compounds 1-3 as it photodeoxygenates and fluoresces when excited with 390 nm. The emission and excitation spectra of 4 are shown in FIG. 2.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:

1. A method for producing ground state atomic oxygen [O($^3$P)] and an oxidation product, the method comprising illuminating a mixture comprising a polycyclic aromatic selenoxide and an oxygen accepting substrate with light to produce ground state atomic oxygen and an oxidation product, wherein the light has a wavelength of from about 370 nm to about 900 nm, wherein the polycyclic aromatic selenoxide has a structure of Formula (Ia), (Ib), (IIa), (IIb), (IIIa), (IIIb), (IVa), or (IVb):

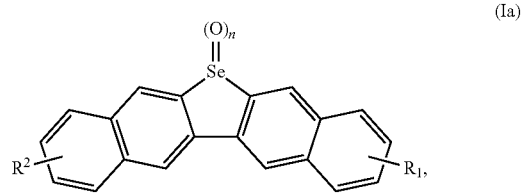

(Ia)

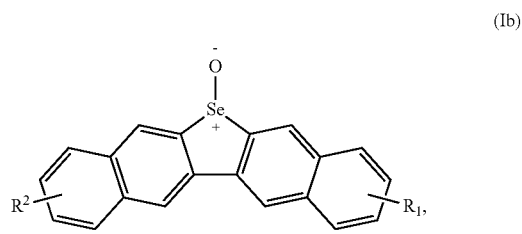

(Ib)

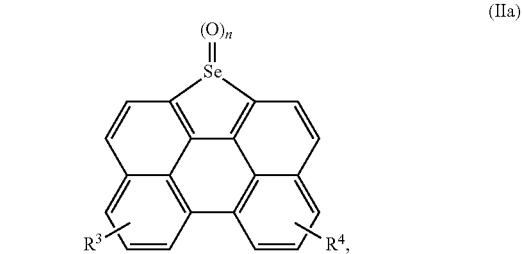

(IIa)

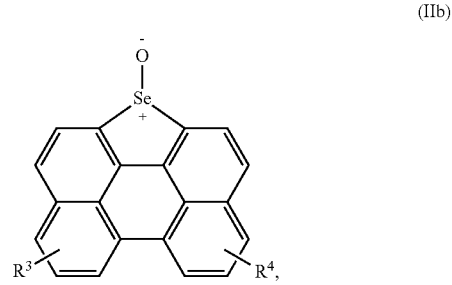

(IIb)

-continued

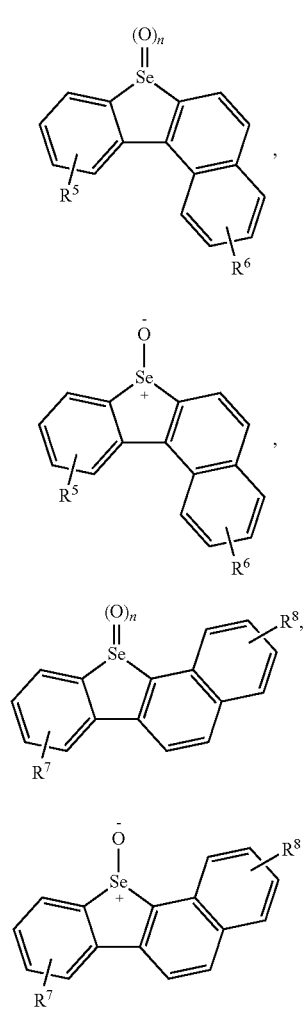

wherein $R^1$, $R^2$, $R^3$, $R^4$, $R^5$, $R^6$, $R^7$ and $R^8$ are each independently hydrogen, hydroxy, substituted or unsubstituted hydrocarbyl, or substituted or unsubstituted amino and n is 1 or 2.

2. The method of claim 1 wherein $R^1$, $R^2$, $R^3$, $R^4$, $R^5$, $R^6$, $R^7$ and $R^8$ are each independently hydrogen, hydroxy, $C_1$-$C_{20}$ alkyl, $C_1$-$C_{20}$ alkoxy, $C_1$-$C_{20}$ haloalkyl, $C_1$-$C_{20}$ haloalkoxy, substituted or unsubstituted $C_2$-$C_{20}$ alkenyl, substituted or unsubstituted $C_2$-$C_{20}$ alkynyl, substituted or unsubstituted aryl, or substituted or unsubstituted heteroaryl.

3. The method of claim 1 wherein $R^1$, $R^2$, $R^3$, $R^4$, $R^5$, $R^6$, $R^7$ and $R^8$ are each independently hydrogen, hydroxy, $C_1$-$C_{10}$ alkyl, $C_1$-$C_{10}$ alkoxy, $C_1$-$C_{10}$ haloalkyl, $C_1$-$C_{10}$ haloalkoxy, halo-substituted $C_1$-$C_{10}$ alkenyl, halo-substituted $C_2$-$C_{10}$ alkynyl, aryl, alkyl-substituted aryl, halo-substituted aryl, or hydroxy-substituted aryl.

4. The method of claim 1 wherein $R^1$, $R^2$, $R^3$, $R^4$, $R^5$, $R^6$, $R^7$ and $R^8$ are each independently hydrogen, hydroxy, methyl, ethyl, butyl, methoxy, ethoxy, propoxy, trifluoromethyl, phenyl, hydroxyphenyl, ethylphenyl, carboxyphenyl, napthyl, anthracenyl, biphenyl, tolyl, cumyl, styryl, ortho-xylyl, meta-xylyl, para-xylyl, fluorophenyl, chlorophenyl, bromophenyl, or iodobenzyl.

5. The method of claim 1 wherein $R^1$, $R^2$, $R^3$, $R^4$, $R^5$, $R^6$, $R^7$ and $R^8$ are each hydrogen.

6. The method of claim 1 wherein n is 1.

7. The method of claim 1 wherein the polycyclic aromatic selenoxide is:

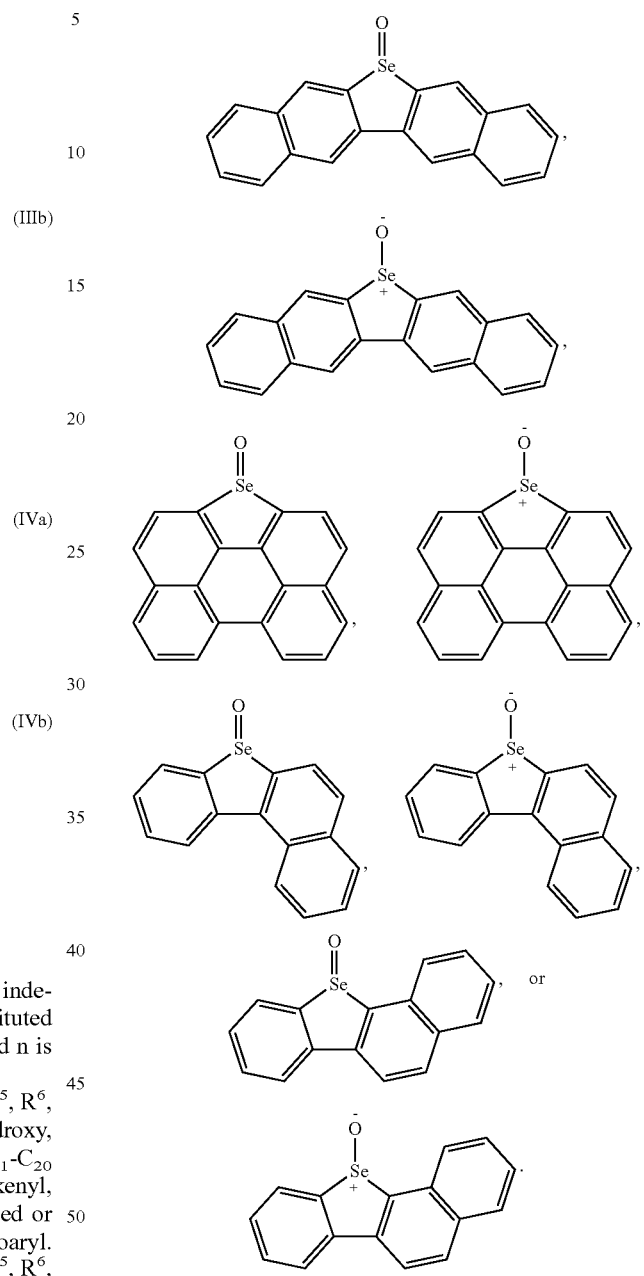

8. The method of claim 1 wherein the mixture is illuminated with light having a wavelength of from about 390 nm to about 740 nm.

9. The method of claim 1 wherein the oxygen accepting substrate comprises a biological specimen, nucleic acid, DNA, RNA, or a protein.

10. The method of claim 1 wherein the oxygen accepting substrate comprises an unsaturated hydrocarbon, an aromatic compound, or a thiol.

11. The method of claim 1, further comprising contacting the mixture with a cell, tissue, or other living system prior to illumination.

12. A compound of Formula (Ia) or (Ib):

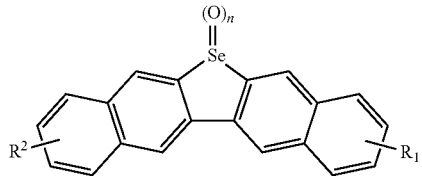
(Ia)

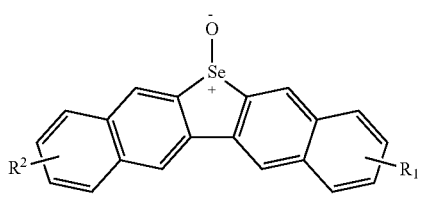
(Ib)

wherein $R^1$ and $R^2$ are each independently hydrogen, hydroxyl, substituted or unsubstituted hydrocarbyl, or substituted or unsubstituted amino and n is 1 or 2.

13. The compound of claim 12 wherein each $R^1$ and $R^2$ are independently hydrogen, hydroxy, $C_1$-$C_{20}$ alkyl, $C_1$-$C_{20}$ alkoxy, $C_1$-$C_{20}$ haloalkyl, $C_1$-$C_{20}$ haloalkoxy, substituted or unsubstituted $C_2$-$C_{20}$ alkenyl, or substituted or unsubstituted $C_2$-$C_{20}$ alkynyl, substituted or unsubstituted aryl, or substituted or unsubstituted heteroaryl.

14. The compound of claim 12 wherein $R^1$ and $R^2$ are each hydrogen.

15. A compound of Formula (IIa) or (IIb):

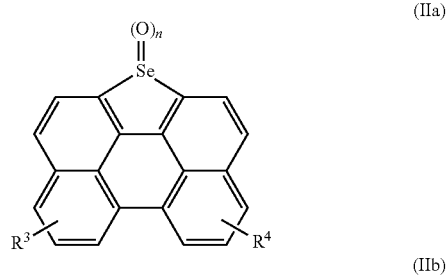
(IIa)

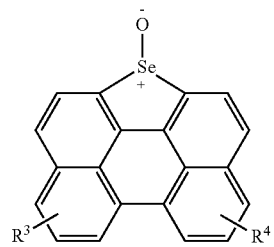
(IIb)

wherein $R^3$ and $R^4$ are each independently hydrogen, hydroxyl, substituted or unsubstituted hydrocarbyl, or substituted or unsubstituted amino and n is 1 or 2.

16. The compound of claim 15 wherein each $R^3$ and $R^4$ are independently hydrogen, hydroxy, $C_1$-$C_{20}$ alkyl, $C_1$-$C_{20}$ alkoxy, $C_1$-$C_{20}$ haloalkyl, $C_1$-$C_{20}$ haloalkoxy, substituted or unsubstituted $C_2$-$C_{20}$ alkenyl, or substituted or unsubstituted $C_2$-$C_{20}$ alkynyl, substituted or unsubstituted aryl, or substituted or unsubstituted heteroaryl.

17. The compound of claim 16 wherein $R^3$ and $R^4$ are each hydrogen.

18. The compound of claim 16 wherein n is 1.

* * * * *